US009901587B2

(12) United States Patent
Bhalani et al.

(10) Patent No.: US 9,901,587 B2
(45) Date of Patent: *Feb. 27, 2018

(54) TOPICAL FILM DELIVERY SYSTEM

(71) Applicant: Sidmak Laboratories (India) Pvt. Ltd., Valsad, Gujarat (IN)

(72) Inventors: Vinayak T. Bhalani, Lutz, FL (US); Anjan Kumar Paul, Valsad (IN); Ashim Kumar Sarkar, Alipurduar (IN)

(73) Assignee: Sidmak Laboratories (India) PVT. LTD., Valsad (IN)

( * ) Notice: Subject to any disclaimer, the term of this patent is extended or adjusted under 35 U.S.C. 154(b) by 0 days.

This patent is subject to a terminal disclaimer.

(21) Appl. No.: 14/921,798

(22) Filed: Oct. 23, 2015

(65) Prior Publication Data
US 2017/0049712 A1    Feb. 23, 2017

Related U.S. Application Data

(63) Continuation of application No. 14/828,184, filed on Aug. 17, 2015.

(51) Int. Cl.
| *A61K 31/65* | (2006.01) |
| *A61K 9/00* | (2006.01) |
| *A61K 9/70* | (2006.01) |
| *A61K 31/167* | (2006.01) |
| *A61K 31/196* | (2006.01) |
| *A61K 31/202* | (2006.01) |
| *A61K 31/203* | (2006.01) |
| *A61K 31/465* | (2006.01) |
| *A61K 31/496* | (2006.01) |
| *A61K 9/06* | (2006.01) |
| *A61K 47/10* | (2017.01) |
| *A61K 47/14* | (2017.01) |
| *A61K 47/32* | (2006.01) |
| *A61K 47/36* | (2006.01) |

(52) U.S. Cl.
CPC ............ *A61K 31/65* (2013.01); *A61K 9/0014* (2013.01); *A61K 9/7015* (2013.01); *A61K 31/167* (2013.01); *A61K 31/196* (2013.01); *A61K 31/202* (2013.01); *A61K 31/203* (2013.01); *A61K 31/465* (2013.01); *A61K 31/496* (2013.01); *A61K 9/06* (2013.01); *A61K 47/10* (2013.01); *A61K 47/14* (2013.01); *A61K 47/32* (2013.01); *A61K 47/36* (2013.01)

(58) Field of Classification Search
CPC .... A61K 9/00141; A61K 47/32; A61K 47/14; A61K 47/10; A61K 31/65; A61K 31/496; A61K 47/36; A61K 31/203; A61K 31/202; A61K 31/196; A61K 31/167; A61K 9/7015; A61K 9/06; A61K 31/465
USPC .............................................................. 1/1
See application file for complete search history.

(56) References Cited

U.S. PATENT DOCUMENTS

| 5,578,310 | A | 11/1996 | M'Timkulu et al. |
| 6,562,363 | B1 * | 5/2003 | Mantelle ............. A61K 9/0014 424/434 |
| 8,663,687 | B2 * | 3/2014 | Myers ................. A61K 8/0208 424/400 |
| 2003/0130427 | A1 | 7/2003 | Cleary |
| 2005/0220831 | A1 | 10/2005 | Jorsal |
| 2009/0169602 | A1 * | 7/2009 | Senti .................. A61B 10/0035 424/448 |
| 2013/0267587 | A1 | 10/2013 | Gonzalez Ojer et al. |
| 2014/0186279 | A1 * | 7/2014 | Joabsson ............. A61K 9/0014 424/59 |
| 2014/0315995 | A1 * | 10/2014 | Dreher ................ A61K 31/375 514/458 |

FOREIGN PATENT DOCUMENTS

WO    2014027006 A1    2/2014

OTHER PUBLICATIONS

Saylor C., et al., "Monoclonal antibody-based therapies for microbial diseases", Vaccine, 2009, pp. 1-20, National Institute of Health.
Dermal Exposure Assessment: Principles and Applications, EPA/600/8-91/011b, Jan. 1992, Interim Report—Exposure Assessment Group, Office of Health and Environmental Assessment, U.S. Environmental Protection Agency, Washington, D.C.

(Continued)

*Primary Examiner* — Robert Cabral
(74) *Attorney, Agent, or Firm* — McCarter & English LLP

(57) ABSTRACT

The described invention provides a topical bioadhesive film-forming pharmaceutical composition formulated for application directly to skin or to a substrate. The composition includes a therapeutic amount of an active agent; and one or more excipients selected from the group consisting of a non-cellulosic polymer or copolymer, a film forming agent, a plasticizer, a permeation enhancer, an antioxidant, a preservative, a solubilizer, a phase transfer catalyst, a viscosity modifier, a vitamin, a mineral nutrient, a solvent, a colorant and a fragrance. It further provides a delivery system comprising the composition and a means for administering the composition. It also describes uses of the delivery system in the manufacture of a medicament for treating a skin condition, disease or disorder, and a method for treating a skin condition, disease or disorder with the composition. The composition is characterized by: controlled release. The formed film is characterized by: locally sustained levels of a minimum effective concentration (MEC) of the active agent between applications; its adherence and conformance to a surface of the skin; its pliability, its resistance to breaking under tension (tensile strength); maintained potency of the active agent; and removability of the film from the skin without a residue.

19 Claims, 3 Drawing Sheets

(56) References Cited

OTHER PUBLICATIONS

Cunningham W.J., "Cosmeceuticals in Photoaging" Cosmeceuticals and Active Cosmetics. Drugs Versus Cosmetics, 2005 pp. 261-277, vol. 27, Taylor & Francis Group, Boca Raton.
Cotta-Pereira G., et al., "Oxytalan, elaunin, and elastic fibers in the human skin", The Journal of Investigative Dermatology, 1976, pp. 143-148, vol. 66.
Shaikh R., et al., "Mucadhesive drug delivery system", J. Pharm. Bioallied Science, 2011, pp. 89-100, vol. 3.
Roge A.B., et al., "Bioadhesive polymer: A review", J. Pharmaceutical & Biomed. Sci., 2011, pp. 1-5, vol. 5.
Hovgaard, L., et al., "Drug delivery studies in Caco-2 monolayers. IV. Absorption enhancer effects of cyclodestrins", Pharmaceutical Research, 1998, pp. 1328-1332, vol. 12, Springer.
Schipper, N.G.M., et al., "Nasal administration of an ACTH (4-9) peptide analogue with dimethyl-b-cyclodextrin as an absorption enhancer: pharmacokinetics and dynamics", Br. J. Pharmacol, 1993, pp. 1335-1340, Macmillan Press Ltd.
Goodman & Gilman's, The Pharmacological Basis of Therapeutics, 2001, pp. 25, 50, McGraw Hill, New York.
Kang, H.K, et al., "Marine peptides and their anti-infective activities", Marine Drugs, 2015, pp. 618-654, vol. 13.
Malkoski, M., "Kappacin, a novel antibacterial peptide from bovine milk", Antimicrobial Agents and Chemotherapy, 2001, pp. 2309-2315, vol. 45, American Society for Microbiology.
Strub, J., et al., "Antibacterial activity of glycosylated and phosporylated chromogranin A-derived peptide 173-194 from bovine adrenal medullary chromaffin granules", The Journal of Biological Chemistry, 1996, pp. 28533-28540, vol. 271, http://www.jbc.org.

\* cited by examiner

TOPICAL FILM DELIVERY SYSTEM

CROSS-REFERENCE TO RELATED APPLICATIONS

This application is a continuation of U.S. application Ser. No. 14/828,184 (filed Aug. 17, 2015), the contents of which are incorporated by reference in their entirety.

FIELD OF THE INVENTION

The described invention relates to topical film formulations and a delivery system for administering same

BACKGROUND OF THE INVENTION

1. Anatomy and Physiology of the Skin

The skin is the largest organ in the body consisting of several layers and plays an important role in biologic homeostasis, and is comprised of the epidermis and the dermis. The epidermis, which is composed of several layers beginning with the stratum corneum, is the outermost layer of the skin, and the innermost skin layer is the deep dermis. The skin has multiple functions, including thermal regulation, metabolic function (vitamin D metabolism), and immune functions. FIG. 1 presents a diagram of skin anatomy.

In humans, the usual thickness of the skin is from 1-2 mm, although there is considerable variation in different parts of the body. The relative proportions of the epidermis and dermis also vary, and a thick skin is found in regions where there is a thickening of either or both layers. For example, on the interscapular (between the shoulder blades) region of the back, where the dermis is particularly thick, the skin may be more than 5 mm thick, whereas on the eyelids it may be less than 0.5 mm. Generally, the skin is thicker on the dorsal or extensor surfaces of the body than on the ventral or flexor surfaces; however, this is not the case for the hands and feet. The skin of the palms and soles is thicker than on any dorsal surface except the intrascapular region. The palms and soles have a characteristically thickened epidermis, in addition to a thick dermis.

The entire skin surface is traversed by numerous fine furrows, which run in definite directions and cross each other to bound small rhomboid or rectangular fields. These furrows correspond to similar ones on the surface of the dermis so that, in section, the boundary line between epidermis and dermis appears wavy. On the thick skin of the palms and soles, the fields form long, narrow ridges separated by parallel coursing furrows, and in the fingertips these ridges are arranged in the complicated loops, whorls (verticil) and spirals that give the fingerprints characteristic for each individual. These ridges are more prominent in those regions where the epidermis is thickest.

Where there is an epidermal ridge externally there is a corresponding narrower projection, called a "rete peg," on the dermal surface. Dermal papillae on either side of each rete peg project irregularly into the epidermis. In the palms and soles, and other sensitive parts of the skin, the dermal papillae are numerous, tall and often branched, and vary in height (from 0.05 mm to 0.2 mm). Where mechanical demands are slight and the epidermis is thinner, such as on the abdomen and face, the papillae are low and fewer in number.

Epidermis

The epidermis provides the body's buffer zone against the environment. It provides protection from trauma, excludes toxins and microbial organisms, and provides a semi-permeable membrane, keeping vital body fluids within the protective envelope. Traditionally, the epidermis has been divided into several layers, of which two represent the most significant ones physiologically. The basal-cell layer, or germinative layer, is of importance because it is the primary source of regenerative cells. In the process of wound healing, this is the area that undergoes mitosis in most instances. The upper epidermis, including stratum and granular layer, is the other area of formation of the normal epidermal-barrier function.

Stratum Corneum and the Acid Mantle

Stratum corneum is an avascular, multilayer structure that functions as a barrier to the environment and prevents transepidermal water loss. Recent studies have shown that enzymatic activity is involved in the formation of an acid mantle in the stratum corneum. Together, the acid mantle and stratum corneum make the skin less permeable to water and other polar compounds, and indirectly protect the skin from invasion by microorganisms. Normal surface skin pH is between 4 and 6.5 in healthy people; it varies according to area of skin on the body. This low pH forms an acid mantle that enhances the skin barrier function.

Other Layers of the Epidermis

Other layers of the epidermis below the stratum corneum include the stratum lucidum, stratum *granulosum*, stratum germinativum, and stratum basale. Each contains living cells with specialized functions (FIG. 2). For example melanin, which is produced by melanocytes in the epidermis, is responsible for the color of the skin. Langerhans cells are involved in immune processing.

Dermal Appendages

Dermal appendages, which include hair follicles, sebaceous and sweat glands, fingernails, and toenails, originate in the epidermis and protrude into the dermis hair follicles and sebaceous and sweat glands contribute epithelial cells for rapid reepithelialization of wounds that do not penetrate through the dermis (termed partial-thickness wounds). The sebaceous glands are responsible for secretions that lubricate the skin, keeping it soft and flexible. They are most numerous in the face and sparse in the palm of the hands and soles of the feet. Sweat gland secretions control skin pH to prevent dermal infections. The sweat glands, dermal blood vessels, and small muscles in the skin (responsible for goose pimples) control temperature on the surface of the body. Nerve endings in the skin include receptors for pain, touch, heat, and cold. Loss of these nerve endings increases the risk for skin breakdown by decreasing the tolerance of the tissue to external forces.

The basement membrane both separates and connects the epidermis and dermis. When epidermal cells in the basement membrane divide, one cell remains, and the other migrates through the granular layer to the surface stratum corneum. At the surface, the cell dies and forms keratin. Dry keratin on the surface is called scale. Hyperkeratosis (thickened layers of keratin) is found often on the heels and indicates loss of sebaceous gland and sweat gland functions if the patient is diabetic. The basement membrane atrophies with aging; separation between the basement membrane and dermis is one cause for skin tears in the elderly.

Dermis

The dermis, or the true skin, is a vascular structure that supports and nourishes the epidermis. In addition, there are sensory nerve endings in the dermis that transmit signals regarding pain, pressure, heat, and cold. The dermis is divided into two layers: the superficial dermis and the deep dermis.

The superficial dermis consists of extracellular matrix (collagen, elastin, and ground substances) and contains blood vessels, lymphatics, epithelial cells, connective tissue, muscle, fat, and nerve tissue. The vascular supply of the dermis is responsible for nourishing the epidermis and regulating body temperature. Fibroblasts are responsible for producing the collagen and elastin components of the skin that give it turgor. Fibronectin and hyaluronic acid are secreted by the fibroblasts. The structural integrity of the dermis plays a role in the normal function and youthful appearance of the skin.

The deep dermis is located over the subcutaneous fat; it contains larger networks of blood vessels and collagen fibers to provide tensile strength. It also consists of fibroelastic connective tissue, which is yellow and composed mainly of collagen. Fibroblasts are also present in this tissue layer. The well-vascularized dermis withstands pressure for longer periods of time than subcutaneous tissue or muscle. The collagen in the skin gives the skin its toughness. Dermal wounds, e.g., cracks or pustules, involve the epidermis, basal membrane, and dermis. Typically, dermal injuries heal rapidly.

2. Effects of Application to the Skin

Substances are applied to the skin to elicit one or more of four general effects: an effect on the skin surface, an effect within the stratum corneum; an effect requiring penetration into the epidermis and dermis; or a systemic effect resulting from delivery of sufficient amounts of a given substance through the epidermis and the dermis to the vasculature to produce therapeutic systemic concentrations. One example of an effect on the skin surface is formation of a film. Film formation may be protective (e.g., sunscreen) and/or occlusive (e.g., to provide a moisturizing effect by diminishing loss of moisture from the skin surface). One example of an effect within the stratum corneum is skin moisturization; which may involve the hydration of dry outer cells by surface films or the intercalation of water in the lipid-rich intercellular laminae; the stratum corneum also may serve as a reservoir phase or depot wherein topically applied substances accumulate due to partitioning into, or binding with, skin components.

It generally is recognized that short-term penetration occurs through the hair follicles and the sebaceous apparatus of the skin, while long term penetration occurs across cells. Penetration of a substance into the viable epidermis and dermis may be difficult to achieve, but once it has occurred, the continued diffusion of the substance into the dermis is likely to result in its transfer into the microcirculation of the dermis and then into the general circulation. It is possible, however, to formulate delivery systems that provide substantial localized delivery.

Percutaneous absorption is the absorption of substances from outside the skin to positions beneath the skin, including into the blood stream. The epidermis of human skin is highly relevant to absorption rates. Passage through the stratum corneum marks the rate-limiting step for percutaneous absorption. The major steps involved in percutaneous absorption of, for example, a drug include the establishment of a concentration gradient, which provides a driving force for drug movement across the skin, the release of drug from the vehicle into the skin-partition coefficient and drug diffusion across the layers of the skin-diffusion coefficient. The relationship of these factors to one another is summarized by the following equation:

$$J = C_{veh} \times K_m \cdot D/x \qquad \text{[Formula 1]}$$

where J=rate of absorption; $C_{veh}$=concentration of drug in vehicle; $K_m$=partition coefficient; and D=diffusion coefficient.

The many factors that affect the rate of percutaneous absorption of a substance include, without limitation, the following: (i) Concentration. The more concentrated the substance, the greater the absorption rate. (ii) Size of skin surface area. The wider the contact area of the skin to which the substance is applied, the greater the absorption rate. (iii) Anatomical site of application. Skin varies in thickness in different areas of the body. A thicker and more intact stratum corneum decreases the rate of absorbency of a substance. The stratum corneum of the facial area is much thinner than, for example, the skin of the palms of the hands. The facial skin's construction and the thinness of the stratum corneum provide an area of the body that is optimized for percutaneous absorption to allow delivery of active agents both locally and systemically through the body. (iv) Hydration. Hydration (meaning increasing the water content of the skin) causes the stratum corneum to swell which increases permeability. (v) Skin temperature. Increased skin temperature increases permeability. (vi) Composition. The composition of the compound and of the vehicle also determines the absorbency of a substance.

Most substances applied topically are incorporated into bases or vehicles. The vehicle chosen for a topical application will greatly influence absorption, and may itself have a beneficial effect on the skin. Factors that determine the choice of vehicle and the transfer rate across the skin are the substance's partition coefficient, molecular weight and water solubility. The protein portion of the stratum corneum is most permeable to water soluble substances and the lipid portion of the stratum corneum is most permeable to lipid soluble substances. It follows that substances having both lipid and aqueous solubility may traverse the stratum corneum more readily. (See Dermal Exposure Assessment: Principles and Applications, EPA/600/8-91/011b, January 1992, Interim Report—Exposure Assessment Group, Office of Health and Environmental Assessment, U.S. Environmental Protection Agency, Washington, D.C. 20460).

3. Wound Healing

The term "wound healing" refers to the process by which the body repairs trauma to any of its tissues, especially those caused by physical means and with interruption of continuity. The term "wound healing agent" refers to any substance that facilitates in the wound healing process.

A wound-healing response often is described as having three distinct phases-injury, inflammation and repair. Generally speaking, the body responds to injury with an inflammatory response, which is crucial to maintaining the health and integrity of an organism. If however it goes awry, it can result in tissue destruction.

Phase I: Injury

Injury caused by factors including, but not limited to, autoimmune or allergic reactions, environmental particulates, infection or mechanical damage often results in the disruption of normal tissue architecture, initiating a healing response. Damaged epithelial and endothelial cells must be replaced to maintain barrier function and integrity and prevent blood loss, respectively. Acute damage to endothelial cells leads to the release of inflammatory mediators and initiation of an anti-fibrinolytic coagulation cascade, temporarily plugging the damaged vessel with a platelet and fibrin-rich clot. For example, lung homogenates, epithelial cells or bronchoalveolar lavage fluid from idiopathic pulmonary fibrosis (IPF) patients contain greater levels of the platelet-differentiating factor, X-box-binding protein-1, compared with chronic obstructive pulmonary disease (COPD) and control patients, suggesting that clot-forming responses are continuously activated. In addition, thrombin (a serine protease required to convert fibrinogen into fibrin) is also readily detected within the lung and intra-alveolar spaces of several pulmonary fibrotic conditions, further confirming the activation of the clotting pathway. Thrombin also can directly activate fibroblasts, increasing proliferation and promoting fibroblast differentiation into collagen-producing myofibroblasts. Damage to the airway epithelium, specifically alveolar pneumocytes, can evoke a similar anti-fibrinolytic cascade and lead to interstitial edema, areas of acute inflammation and separation of the epithelium from the basement membrane.

Platelet recruitment, degranulation and clot formation rapidly progress into a phase of vasoconstriction with increased permeability, allowing the extravasation (movement of white blood cells from the capillaries to the tissues surrounding them) and direct recruitment of leukocytes to the injured site. The basement membrane, which forms the extracellular matrix underlying the epithelium and endothelium of parenchymal tissue, precludes direct access to the damaged tissue. To disrupt this physical barrier, zinc-dependent endopeptidases, also called matrix metalloproteinases (MMPs), cleave one or more extracellular matrix constituents allowing extravasation of cells into, and out of, damaged sites. Specifically, MMP-2 (gelatinase A, Type N collagenase) and MMP-9 (gelatinase B, Type IV collagenase) cleave type N collagens and gelatin, two important constituents of the basement membrane. Recent studies have found that MMP-2 and MMP-9 are upregulated, highlighting that tissue-destructive and regenerative processes are common in fibrotic conditions. The activities of MMPs are controlled by several mechanisms including transcriptional regulation, proenzyme regulation, and specific tissue inhibitors of MMPs. The balance between MMPs and the various inhibitory mechanisms can regulate inflammation and determine the net amount of collagen deposited during the healing response.

Previous studies using a model of allergic airway inflammation and remodeling with MMP-2−/−, MMP-9−/− and MMP-2−/−MMP-9−/− double knockout mice showed that MMP-2 and MMP-9 were required for successful egression and clearance of inflammatory cells out of the inflamed tissue and into the airspaces. In the absence of these MMPs, cells were trapped within the parenchyma of the lung and were not able to move into the airspaces, which resulted in fatal asphyxiation.

Phase II: Inflammation

Once access to the site of tissue damage has been achieved, chemokine gradients recruit inflammatory cells. Neutrophils, eosinophils, lymphocytes, and macrophages are observed at sites of acute injury with cell debris and areas of necrosis cleared by phagocytes.

The early recruitment of eosinophils, neutrophils, lymphocytes, and macrophages providing inflammatory cytokines and chemokines can contribute to local TGF-β and IL-13 accumulation. Following the initial insult and wave of inflammatory cells, a late-stage recruitment of inflammatory cells may assist in phagocytosis, in clearing cell debris, and in controlling excessive cellular proliferation, which together may contribute to normal healing. Late-stage inflammation may serve an anti-fibrotic role and may be required for successful resolution of wound-healing responses. For example, a late-phase inflammatory profile rich in phagocytic macrophages, assisting in fibroblast clearance, in addition to IL-10-secreting regulatory T cells, suppressing local chemokine production and TGF-β, may prevent excessive fibroblast activation.

The nature of the insult or causative agent often dictates the character of the ensuing inflammatory response. For example, exogenous stimuli like pathogen-associated molecular patterns (PAMPs) are recognized by pathogen recognition receptors, such as toll-like receptors and NOD-like receptors (cytoplasmic proteins that have a variety of functions in regulation of inflammatory and apoptotic responses), and influence the response of innate cells to invading pathogens. Endogenous danger signals also can influence local innate cells and orchestrate the inflammatory cascade.

The nature of the inflammatory response dramatically influences resident tissue cells and the ensuing inflammatory cells. Inflammatory cells themselves also propagate further inflammation through the secretion of chemokines, cytokines, and growth factors. Many cytokines are involved throughout a wound-healing and fibrotic response, with specific groups of genes activated in various conditions. For example, chronic allergic airway disease in asthmatics is associated commonly with elevated type-2 helper T cell (Th2) related cytokine profiles (including, but not limited to, interleukin-4 (IL-4), interleukin-5 (IL-5), interleukin-6 (IL-6), interleukin-13 (IL-13), and interleukin-9 (IL-9)), whereas chronic obstructive pulmonary disease and fibrotic lung disease (such as idiopathic pulmonary fibrosis) patients more frequently present pro-inflammatory cytokine profiles (including, but not limited to, interleukin-1 alpha (IL-1α), interleukin-1 beta (IL-1β), interleukin-6 (IL-6), tumor necrosis factor alpha (TNF-α), transforming growth factor beta (TGF-β), and platelet-derived growth factors (PDGFs)). Each of these cytokines has been shown to exhibit significant pro-fibrotic activity, acting through the recruitment, activation and proliferation of fibroblasts, macrophages, and myofibroblasts.

Phase III: Tissue Repair and Contraction

The closing phase of wound healing consists of an orchestrated cellular re-organization guided by a fibrin (a fibrous protein that is polymerized to form a "mesh" that forms a clot over a wound site)-rich scaffold formation, wound contraction, closure and re-epithelialization. The vast majority of studies elucidating the processes involved in this phase of wound repair have come from dermal wound studies and in vitro systems.

Myofibroblast-derived collagens and smooth muscle actin (α-SMA) form the provisional extracellular matrix, with macrophage, platelet, and fibroblast-derived fibronectin forming a fibrin scaffold. Collectively, these structures are commonly referred to as granulation tissues. Primary fibroblasts or alveolar macrophages isolated from idiopathic pulmonary fibrosis patients produce significantly more fibronectin and α-SMA than control fibroblasts, indicative of a state of heightened fibroblast activation. It has been reported that IPF patients undergoing steroid treatment had similar elevated levels of macrophage-derived fibronectin as IPF patients without treatment. Thus, similar to steroid resistant IL-13-mediated myofibroblast differentiation, macrophage-derived fibronectin release also appears to be resistant to steroid treatment, providing another reason why steroid treatment may be ineffective. From animal models, fibronectin appears to be required for the development of pulmonary fibrosis, as mice with a specific deletion of an extra type III domain of fibronectin (EDA) developed significantly less fibrosis following bleomycin administration compared with their wild-type counterparts.

In addition to fibronectin, the provisional extracellular matrix consists of glycoproteins (such as PDGF), glycosaminoglycans (such as hyaluronic acid), proteoglycans and elastin. Growth factor and TGF-β-activated fibroblasts migrate along the extracellular matrix network and repair the wound. Within skin wounds, TGF-β also induces a contractile response, regulating the orientation of collagen fibers. Fibroblast to myofibroblast differentiation, as discussed above, also creates stress fibers and the neo-expression of α-SMA, both of which confer the high contractile activity within myofibroblasts. The attachment of myofibroblasts to the extracellular matrix at specialized sites called the "fibronexus" or "super mature focal adhesions" pull the wound together, reducing the size of the lesion during the contraction phase. The extent of extracellular matrix laid down and the quantity of activated myofibroblasts determines the amount of collagen deposition. To this end, the balance of matrix metalloproteinases (MMPs) to tissue inhibitor of metalloproteinases (TIMPs) and collagens to collagenases vary throughout the response, shifting from pro-synthesis and increased collagen deposition towards a controlled balance, with no net increase in collagen. For successful wound healing, this balance often occurs when fibroblasts undergo apoptosis, inflammation begins to subside, and granulation tissue recedes, leaving a collagen-rich lesion. From skin studies, re-epithelialization of the wound site re-establishes the barrier function and allows encapsulated cellular re-organization. Several in vitro and in vivo models, using human or rat epithelial cells grown over a collagen matrix, or tracheal wounds in vivo, have been used to identify significant stages of cell migration, proliferation, and cell spreading. Rapid and dynamic motility and proliferation, with epithelial restitution from the edges of the denuded area occur within hours of the initial wound. In addition, sliding sheets of epithelial cells can migrate over the injured area assisting wound coverage. Several factors have been shown to regulate re-epithelialization, including serum-derived transforming growth factor alpha (TGF-α), and matrix metalloproteinase-7 (MMP-7) (which itself is regulated by TIMP-1).

4. Delivery Systems for Topical Administration

Many active agents are administrated enterally or parenterally. Enteral routes of administration involve administration to any part of the gastrointestinal tract, typically via oral forms, e.g., pills, tablets, emulsions, and syrups, or via rectal forms, e.g., enemas, Murphy drips, and suppositories. Parenteral routes of administration involve administration by some means other than oral or rectal, typically via injections or infusions. While such administration routes allow for accurate and consistent dosing, such routes necessarily yield systemic effects, e.g., vestibular symptoms, headache and general malaise, and gastrointestinal symptoms, which in certain circumstances are not desirable.

Topical routes of administration involve administration to a body surface, such as the skin, or mucous membranes. Many forms of topical administration involve applying a therapeutic agent directly to the skin; inhalable mediations, eye drops, and ear drops also are considered topical administration forms. Although topical administration generally provides a local effect, many topically administered drugs can exhibit systemic effects, such as vestibular symptoms (e.g., vertigo, dizziness or blurred vision), headache and general malaise, gastro-intestinal symptoms, such as diarrhea, nausea, gas, cramps, dry nose and dry mouth.

Formulations for topical application can take the compositional form of a liquid, a semisolid dosage form (e.g., a paste, a cream, a lotion, a powder, an ointment or a gel) or a patch.

Liquid formulations do not readily stay in place and can be messy. Semisolid formulations offer some advantages characteristic of topical administration, such as ease of application, and increased local doses of active agent, with reduced systemic effects, but their potential disadvantages include the need for repeated application, difficulties in accurate dosing, and messy or unattractive cosmetic attributes, all of which can lead to poor user compliance, and unintentional removal or transfer of active agent via contact with objects or other persons.

Topical patches, which are available in multiple forms including single and multi-layer drug-in-adhesive forms, matrix forms, and reservoir forms, address several of the shortcomings of semisolid formulations, for example, reducing the need for repeated application, providing accurate, and controlled release of active agent, and reducing the likelihood of unintentional removal or transfer of drug or active agent via contact with objects or other persons, but have a finite size and shape. Because topical patches have a finite size and shape, the application area is determined by the dimensions of the patch rather than the dimensions of the affected site. Accordingly, it may be necessary to use a number of patches in order to cover a large affected site. Furthermore, topical patches typically lack sufficient flexibility to be effectively administered to joints or other areas of skin subject to significant stretching movements. Topical patches can also lead to user discomfort, particular in warmer climates, and can be aesthetically unpleasing, which can also lead to poor user compliance.

Several therapeutic formulations in film form have been described. Those that involve thin films on substrates of finite size and shape similar to patches inherit the same disadvantages as for patches, e.g., having the application area determined by the film dimensions rather than the dimensions of the affected site.

The described delivery system, which provides a drug delivery system for controlled delivery of an active agent comprising a pharmaceutical composition that dries to a film form and a means for applying the film, overcomes these shortcomings. The composition in film form has the following advantageous properties: it is long-lasting, i.e., it remains in place over the administration site for the desired time, can be removed by peeling without leaving a substantial residue, is effective to achieve minimum effective concentration (MEC) of the active agent in the layers of the skin while the level of the active in systemic circulation is below therapeutic levels, is nonstaining regardless of the staining properties of the active, and can be applied to an affected site of any size.

SUMMARY OF THE INVENTION

According to one aspect, the described invention provides a topical bioadhesive film-forming pharmaceutical composition for application directly to skin or to a substrate comprising (a) a therapeutic amount of an active agent; and (b) one or more excipients selected from the group consisting of a non-cellulosic polymer or copolymer, a film forming agent, a plasticizer, a permeation enhancer, an antioxidant, a preservative, a solubilizer, a phase transfer catalyst, a viscosity modifier, a vitamin, a mineral nutrient, a solvent, a colorant and a fragrance, the composition being characterized by controlled release; and the resulting film being characterized by: its maintenance of sustained levels of the active agent locally or systemically; its conformance to a surface of the skin without breaking; its pliability; and its removability without leaving a substantial residue. According to one embodiment, the active agent is an analgesic agent, an anesthetic agent; an anti-acne agent; an anti-aging agent, an antibiotic agent; an anti-fungal agent; an antihistamine, an anti-inflammatory agent (steroidal and nonsteroidal); a nicotinic cholinergic receptor agonist, an antioxidant agent; an anti-protozoal agent; an anti-pruritic agent; an anti-viral agent; a chemotherapeutic agent, an immunomodulatory agent, a keratolytic agent, or a retinoid. According to another embodiment, the active agent is an antibiotic. According to another embodiment, the antibiotic is a beta-lactam, a cephalosporin, a fluoroquinolones, an aminoglycoside, a monobactam, a carbapenem, a macrolide, or a tetracycline, a natural or synthetic anti-infective peptide, a glycosylated, phosphorylated, or glycosylated and phosphorylated derivative of a natural or synthetic anti-infective peptide, or an anti-infective monoclonal antibody cocktail. According to another embodiment, the antibiotic is a tetracycline antibiotic. According to another embodiment, the tetracycline antibiotic is minocycline. According to another embodiment, the active agent is an anti-fungal agent. According to another embodiment, the anti-fungal agent is itraconazole. According to another embodiment, the nicotinic cholinergic receptor agonist is nicotine. According to another embodiment, the composition is in form of a gel. According to another embodiment, the retinoid is isotretinoin. According to another embodiment, the non-cellulosic copolymer is selected from the group consisting of a poloxamer, an ethoxylated linear alcohol, a fatty acid ester, an amine derivative, and amide derivative, a polyglucoside, a polyalcohol, an ethoxylated polyalcohol, and a thiol. According to another embodiment, the film forming agent is selected from the group consisting of polyvinyl alcohol, polyvinyl pyrrolidone (copovidone), carrageenan, gelatin, dextrin, polyethylene oxide, guar gum, xanthan gum, Tragacanth gum, polyvinyl alcohol-polyethylene glycol co-polymers, methacrylic acid-ethyl acrylate copolymers, methacrylic acid and methacrylate based polymers, and a methylmethacrylate copolymer. According to another embodiment, the plasticizer is selected from the group consisting of triacetine, triethyl citrate, acetyl triethyl citrate, tributyl citrate, acetyl tributyl citrate, trimethyl citrate, other citrate esters, glycerin, sorbitol, a polyethylene glycol, a polypropylene glycol, a polyethylene-propylene glycol, glycerol, glycerol monoacetate, glycerol diacetate, glycerol polysorbate, cetyl alcohol, and sodium diethylsulfosuccinate. According to another embodiment, the permeation enhancer is selected from the group consisting of isopropyl palmitate, isopropyl myristate, isopropyl stearate, propylene glycol, octyl stearate, tridecyl neopentanoate, benzyl alcohol, linoleic acid, alpha-linolenic, oleic acid, cod-liver-oil, methanol, menthol derivatives, squalene, glycerol derivatives, urea, sodium taurocholate or a combination thereof. According to another embodiment, the antioxidant is selected from the group consisting of alpha tocopherol (Vitamin-E), ascorbic acid, ascorbic acid esters, glutathione, lipoic acid, uric acid, carotenes, propyl gallate, sodium bisulfite, sodium sulfite, butylated hydroxytoluene (BHT), butylated hydroxyanisole (BHA), and cysteine. According to another embodiment, the organic solvent is selected from the group consisting of polyhydric alcohol, glycerin, ethylene glycol, dipropylene glycol, hexylene glycol, and mixtures thereof. According to another embodiment, the active agent is present at a concentration ranging from 1% to 60% w/w, the non-cellulosic copolymer is present at a concentration ranging from 1% to 30% w/w; the film forming agent is present at a concentration ranging from 1% to 80% w/w; the plasticizer is present at a concentration ranging from 1% to 20% w/w; the antioxidant is present at a concentration ranging from 0.1% to 10% w/w; and the hydroalcoholic solvent is present at a concentration ranging from 10% to 90% w/v. According to another embodiment, the substrate is a backing material. According to another embodiment, the backing material is occlusive. According to another embodiment, the backing material is nonocclusive.

According to another aspect, the described invention provides a method for treating a skin condition, disease or disorder in a subject in need thereof comprising applying to the skin of the subject the topical bioadhesive film-forming composition. According to one embodiment, the skin disorder is pruritus, atopic dermatitis, acne, a skin infection, a skin neoplasm, a wound, or a skin manifestation of an autoimmune disorder. According to another embodiment, the active agent is minocycline or isotretinoin, the skin disorder is acne, and the therapeutic amount is effective to treat the acne. According to another embodiment, the active agent is itraconazole, the skin disorder is a fungal infection, and the therapeutic amount is effective to treat the fungal infection.

According to another aspect, the described invention provides a topical delivery system for local delivery of a therapeutic amount of a therapeutic agent to the skin comprising A) a topical bioadhesive film-forming pharmaceutical composition formulated for application directly to skin or to a substrate comprising: (a) a therapeutic amount of an active agent; and (b) one or more excipients selected from the group consisting of a non-cellulosic polymer or copolymer, a film forming agent, a plasticizer, a permeation enhancer, an antioxidant, a preservative, a solubilizer, a phase transfer catalyst, a viscosity modifier, a vitamin, a mineral nutrient, a solvent, a colorant, and a fragrance, the composition being characterized by controlled release, and the formed film being characterized by: its maintenance of sustained levels of the active agent locally or systemically; its conformance to a surface of the skin without breaking; its pliability; and its removal without leaving a substantial residue; and B) a means for delivering the composition to a surface of the skin. According to one embodiment of the delivery system, the means for delivering the composition to a surface of the skin is a delivery apparatus. According to another embodiment, the delivery apparatus comprises a first chamber containing a first component of the composition and a second chamber containing a second component of the composition. According to another embodiment, the first chamber and second chamber are connectively linked. According to another embodiment, the delivery apparatus is an applicator. According to another embodiment, the applicator is an aerosol container, an atomizer, a container with an apical manual pump, a rollette bottle or a tube container. According to another embodiment, the substrate is a backing material. According to another embodiment, the backing material is occlusive. According to another embodiment, the backing material is nonocclusive.

According to another aspect of the described invention, a delivery system for use in the manufacture of a medicament for treating a skin condition, disease or disorder comprises: A) a topical bioadhesive film-forming pharmaceutical composition formulated for application directly to skin or to a substrate comprising: (a) a therapeutic amount of an active agent; and (b) one or more excipients selected from the group consisting of a non-cellulosic polymer or copolymer, a film forming agent, a plasticizer, a permeation enhancer, an antioxidant, a preservative, a solubilizer, a phase transfer catalyst, a viscosity modifier, a vitamin a mineral nutrient, a solvent, a color and a fragrance, the composition being characterized by controlled release; the formed film being characterized by: its maintenance of sustained levels of the active agent locally or systemically; its conformance to a surface of the skin without breaking; its pliability; and its removal without leaving a substantial residue; and B) a means for delivering the composition to a surface of the skin, wherein the therapeutic amount of the active agent is effective to treat the skin disease, disorder or condition. According to one embodiment, the skin disorder is pruritus, atopic dermatitis, acne, a skin infection, a skin neoplasm, a wound, or a skin manifestation of an autoimmune disorder. According to another embodiment, the active agent is minocycline, the skin disorder, is acne, and the therapeutic amount is effective to treat the acne. According to another embodiment, the active agent is itraconazole, the skin disorder is a fungal infection, and the therapeutic amount is effective to treat the fungal infection.

DETAILED DESCRIPTION OF THE INVENTION

Glossary

Figure 1:
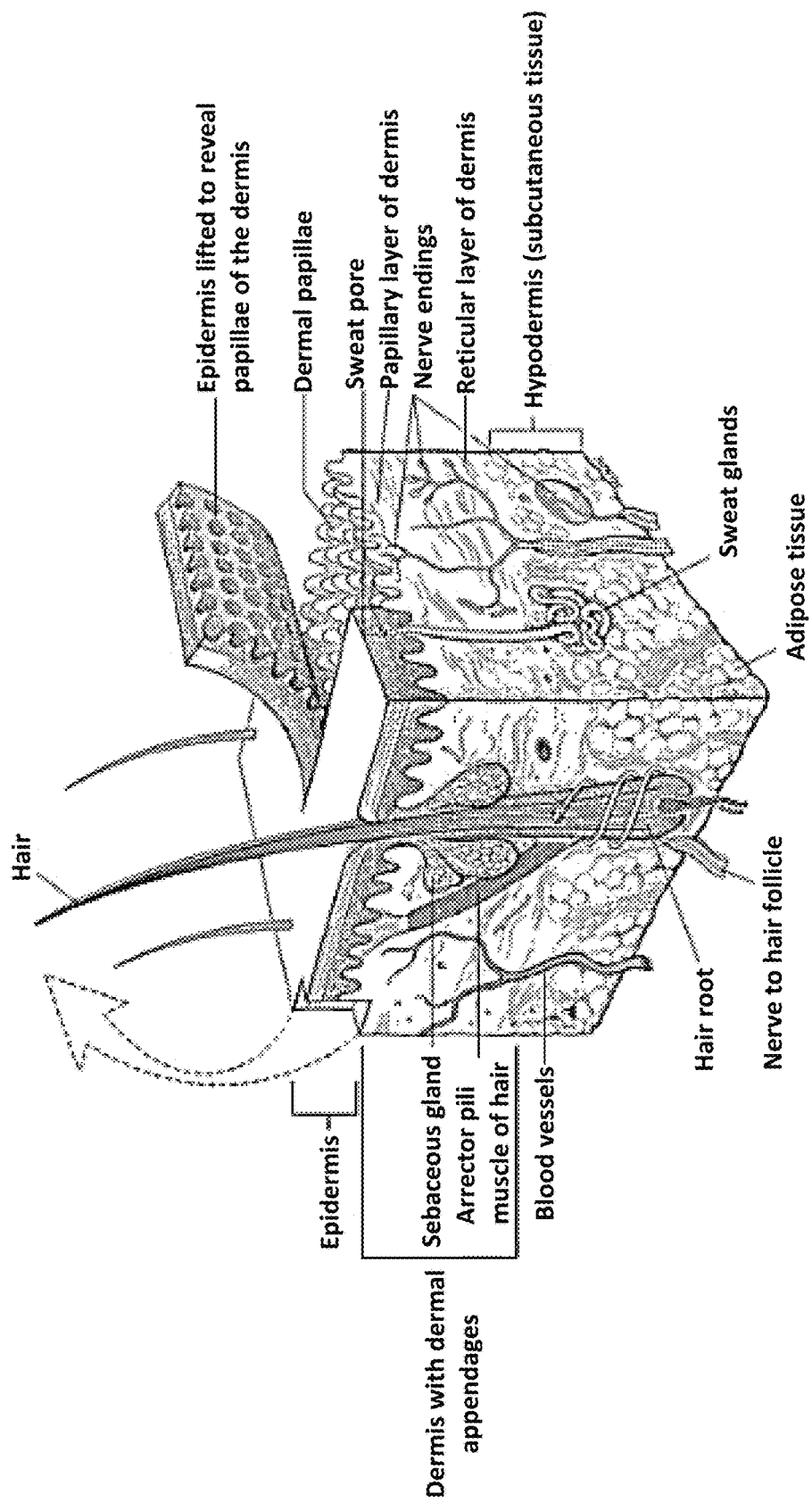
FIG. 1 presents a diagram of skin anatomy. Taken from Stedman's Medical Dictionary, 27th Ed., Lippincott, Williams & Wilkins, Baltimore, Md. (2000), at 1647.
Figure 2:
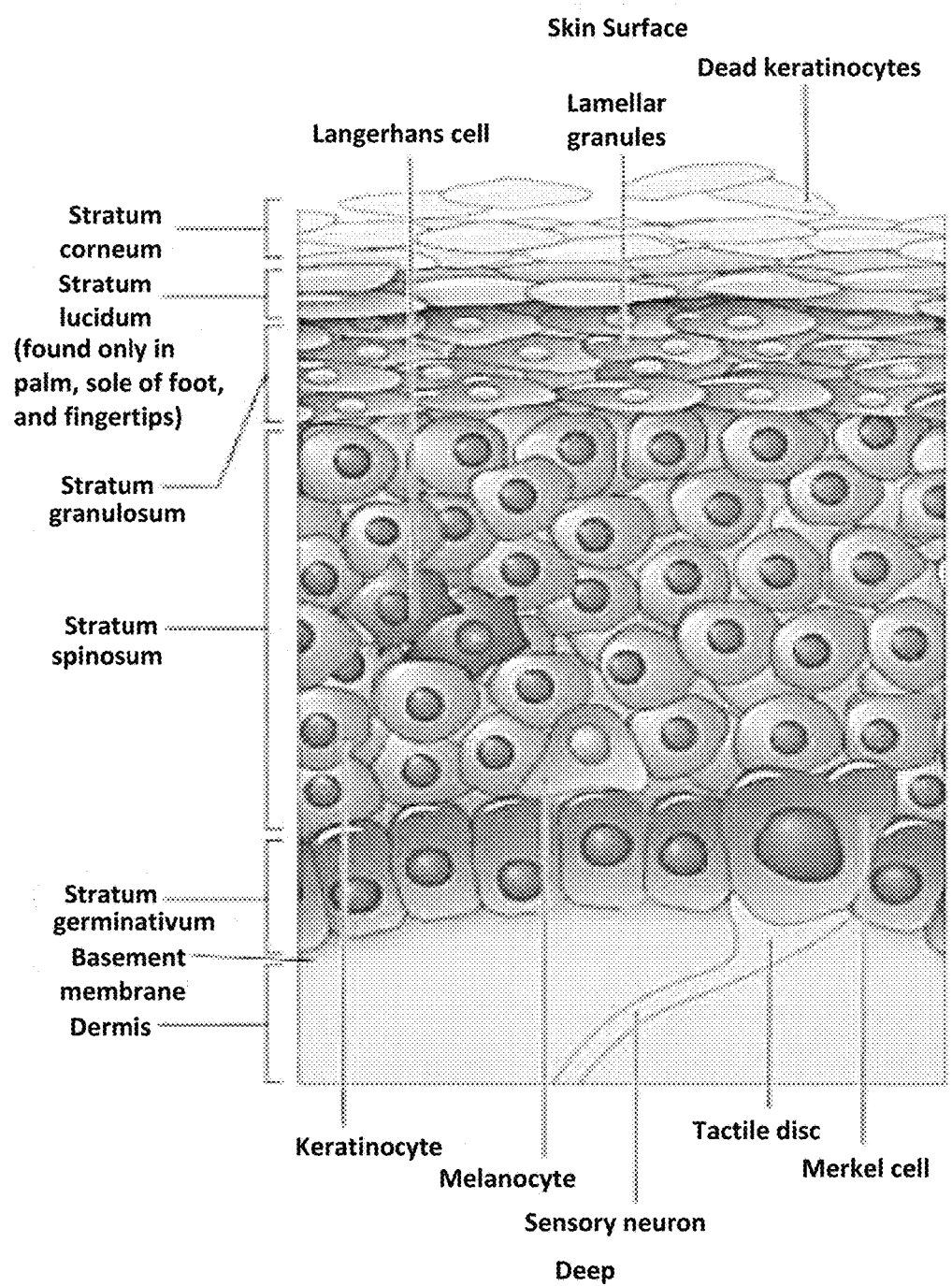
FIG. 2 shows layers of the epidermis.
Figure 3:
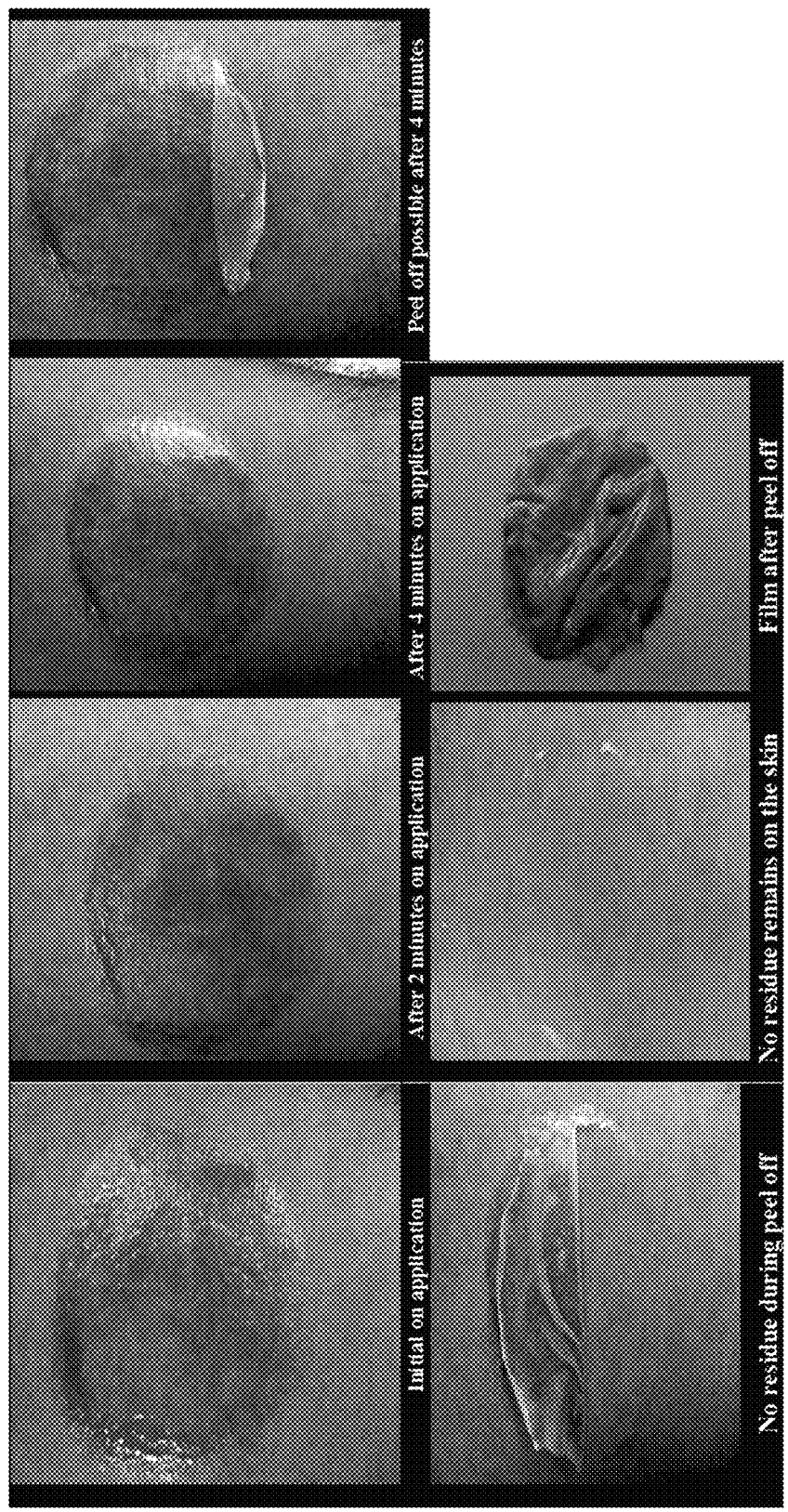
FIG. 3 shows the properties of a topically administered minocycline film.

The term "acne vulgaris" or "acne" refers to a disorder of the skin caused by inflammation of the skin glands and hair follicles, often characterized by areas of blackheads, whiteheads, pimples, greasy skin, and possibly scarring.

The term "active agent" refers to the ingredient, component or constituent of the compositions of the described invention responsible for the intended therapeutic effect.

The term "acute" release, as used herein, means that the topically administered delivery system is constructed and arranged to deliver therapeutic levels of the active agent for at least 1 hour, 2 hours, 3 hours, 4 hours, 5 hours, 6 hours, 7 hours, 8 hours, 9 hours, 10 hours 11 hours, or 12 hours.

The term "adhere" as used herein refers to staying attached, cling to, to be united by a molecular force acting in the area of contact.

The term "administer" as used herein means to give or to apply. The term "administering" as used herein includes in vivo administration, as well as administration directly to tissue ex vivo.

The term "aging skin" as used herein refers to the problem of exposed areas of the skin, such as the face, having the appearance of older skin far earlier than never exposed sites of the body.

Skin aging is a cumulative and multi-factorial process in which both intrinsic and extrinsic determinants lead progressively to a loss of structural integrity and physiological function of the skin. For example, as skin ages, cell renewal can decrease dramatically so skin looks dry and dull.

Intrinsic aging of the skin occurs as a natural consequence of physiological changes over time at variable genetically determined rates. Extrinsic aging is mediated by environmental factors, including, without limitation, exposure to sunlight, pollution, nicotine, repetitive muscle movements, such as squinting or frowning, and miscellaneous lifestyle components, such as diet, sleeping position and overall health.

Youthful skin is characterized by its unblemished, evenly pigmented, and smooth appearance.

Intrinsically aged skin is comparatively thin, inelastic and finely wrinkled with deepening of facial expression lines. These changes are evidenced histologically as a thinned epidermis and dermis with flattening of the rete pegs at the dermo-epidermal junction (DEJ, the intersection of the epidermis and dermis).

Cutaneous aging due to sun exposure is known as photoaging. The rate of change in the skin due to photoaging is dependent on many intrinsic and extrinsic or environmental factors, including, without limitation, genetic background of the individual, environmental latitude at which sun exposure takes place, intensity and duration of sun exposure in outdoor activities of sport, employment or leisure, and to some extent, vigor of prevention or treatment. William J. Cuningham, "Cosmeceuticals in Photoaging" in Cosmeceuticals and Active Cosmetics, Eisner, P. and Maibach, H I, Eds, 2nd Ed., Taylor & Francis Group, Boca Raton (2005) at 263-65. Extrinsically aged, sun-exposed skin appears clinically as blemished, thickened, yellowed, lax, rough, and leathery. These changes may begin as early as the second decade.

Irregular hyperpigmentation and hypopigmentation, both discrete and limited or diffuse and irregular may be noted, and clinically represented by freckles, solar lentigines (blemishes on the skin that range in color from light brown to red or black), and hypomelanotic macules (meaning a flat, distinct, colored area of skin that is less than 1 centimeter in diameter and does not include a change in skin texture or thickness). An appearance and feel of surface roughness, dryness or scaliness may be partially explained by abnormalities of keratinocyte production, adhesion and separation. Wrinkles of various depth, length and location are a reflection of underlying dermal damage to collagen, elastin and ground substance and their incomplete repair. Orientation of deeper wrinkles according to lines of underlying muscular forces may be pronounced. The color of photoaged skin may be sallow in some instances but otherwise is variable due to the irregularity of surface and of reflected light as well as to the variability of total skin thickness, melanin content and distribution, and influence of saturated and unsaturated hemoglobin.

Photoaged skin is characterized histologically by epidermal dysplasia with varying degrees of cytologic atypia, loss of keratinocyte polarity, an inflammatory infiltrate, decreased collagen, increased ground substance and elastosis. Elastosis (accumulation of amorphous elastin material) is characteristic of photo-aged skin. By light microscopy, three different types of fibers are observed in normal human skin: oxytalan, elaunin and elastic fibers. Elaunin fibers are a component of elastic fibers formed from a deposition of elastin between oxytalan fibers. Elastic fibers consisting of microfibrils and an amorphous substance containing elastin, branch and anastomose to form networks and fuse to form fenestrated membranes and elastic laminae. Oxytalan fibers, the most superficial ones, which are located in the papillary dermis are very thin, directed perpendicularly to the dermatoepidermal junction, and are formed by bundles of tubular microfibrils 10 to 12 nm in diameter. Cotta-Pereira, G. et al, "Oxytalan, elaunin, and elastic fibers in the human skin," J. Invest. Dermatol. 66(3): 143-48 (1976). UV exposure induces a thickening and coiling of elastic fibers in the papillary dermis and, with chronic UV exposure, in the reticular dermis. UV-exposed skin manifests a reduction in the number of microfibrils and increases in interfibrillar areas. The initial response of elastic fibers to photodamage is hyperplastic (meaning an abnormal multiplication of cells), resulting in a greater amount of elastic tissue. The level of sun exposure determines the magnitude of the hyperplastic response. In aged elastic fibers, a secondary response to photodamage occurs but is degenerative, with a decrease observed in skin elasticity and resiliency. In aged elastic fibers, a secondary response to photodamage occurs but is degenerative, with a decrease observed in skin elasticity and resiliency.

Photo-aged skin also may accumulate changes to epidermal cell DNA and result in many benign and malignant neoplasms of the skin. These include benign seborrheic keratosis (round or oval skin growths that originate in keratinocytes that appear in various colors from light tan to black), actinic keratosis (a premalignant condition of thick, scaly or crusty patches of skin) and squamous cell carcinoma. Some of the propensity toward cancerous growths may be due to a decrease in Langerhans cells and their function. Aged skin may also contain telangiectasias (small dilated blood vessels) and lentigines (blemishes on the skin that range in color from light brown to red or black).

The term "agonist" as used herein refers to a chemical substance capable of activating a receptor to induce a full or partial pharmacological response. Receptors can be activated or inactivated by either endogenous or exogenous agonists and antagonists, resulting in stimulating or inhibiting a biological response. A physiological agonist is a substance that creates the same bodily responses, but does not bind to the same receptor. An endogenous agonist for a particular receptor is a compound naturally produced by the body which binds to and activates that receptor. A superagonist is a compound that is capable of producing a greater maximal response than the endogenous agonist for the target receptor, and thus an efficiency greater than 100%. This does not necessarily mean that it is more potent than the endogenous agonist, but is rather a comparison of the maximum possible response that can be produced inside a cell following receptor binding. Full agonists bind and activate a receptor, displaying full efficacy at that receptor. Partial agonists also bind and activate a given receptor, but have only partial efficacy at the receptor relative to a full agonist. An inverse agonist is an agent which binds to the same receptor binding-site as an agonist for that receptor and reverses constitutive activity of receptors. Inverse agonists exert the opposite pharmacological effect of a receptor agonist. An irreversible agonist is a type of agonist that binds permanently to a receptor in such a manner that the receptor is permanently activated. It is distinct from a mere agonist in that the association of an agonist to a receptor is reversible, whereas the binding of an irreversible agonist to a receptor is believed to be irreversible. This causes the compound to produce a brief burst of agonist activity, followed by desensitization and internalization of the receptor, which with long-term treatment produces an effect more like an antagonist. A selective agonist is specific for one certain type of receptor.

The term "analgesic" as used herein refers to any member of a group of drugs used to provide relief from pain. Analgesic drugs act in various ways on the peripheral and central nervous systems, and are distinct from anesthetics, which reversibly eliminate sensation.

The term "analog" as used herein refers to a compound having a structure similar to another, but differing from it, for example, in one or more atoms, functional groups, or substructure.

The term "anesthetic agents" as used herein refers to agents that resulting in a reduction or loss of sensation.

The term "anti-acne agent" as used herein refers to any chemical and/or biological agent (e.g., an antimicrobial peptide) that when topically administered at the site of acne, leads to a visible reduction of symptoms associated with the epithelial condition of acne vulgaris.

The term "anti-aging agent" as used herein refers to any substance that treats or reduces at least one anti-aging benefit to the skin. As used herein, such benefits include, without limitation, improving skin appearance and/or feel by providing a smoother, more even appearance and/or feel; increasing the thickness of one or more layers of the skin; improving the elasticity or resiliency of the skin; improving the firmness of the skin; and reducing the dull appearance of skin, improving the hydration status or moisturization of the skin, improving the appearance of fine lines and/or wrinkles, improving skin texture or smoothness, improving skin exfoliation or desquamation, plumping the skin, improving skin barrier properties, improving skin tone, reducing the appearance of redness or skin blotches, and/or improving the brightness, radiancy, or translucency of skin. Retinol is an exemplary anti-aging agent.

The term "antagonist" as used herein refers to a substance that counteracts the effects of another substance.

The term "antibiotic agent" as used herein refers to any of a group of chemical substances having the capacity to inhibit the growth of, or to destroy bacteria, and other microorganisms, used chiefly in the treatment of infectious diseases.

The term "anti-fungal agent" as used herein refers to any of a group of chemical substances having the capacity to inhibit the growth of or to destroy fungi. The term "antihistamine" as used herein refers to a drug that inhibits the action of histamine in the body by blocking the receptors of histamine.

The term "anti-inflammatory agent" as used herein refers to a substance that reduces inflammation and swelling.

The term "anti-oxidant agent" as used herein refers to a substance that inhibits oxidation or reactions promoted by oxygen or peroxides.

The term "anti-protozoal agent" as used herein refers to any of a group of chemical substances having the capacity to inhibit the growth of or to destroy protozoans used chiefly in the treatment of protozoal diseases.

The term "antipruritic agents" as used herein refers to those substances that reduce, eliminate or prevent itching. The term "anti-viral agent" as used herein means any of a group of chemical substances having the capacity to inhibit the replication of or to destroy viruses used chiefly in the treatment of viral diseases.

The term "apply" as used herein refers to placing in contact with or to lay or spread on.

The term "applicator" as used herein refers to a device used for applying a substance to a surface.

The term "bioadhesive" is used hereinto refer to a material that possesses the property of bioadhesion. The term "bioadhesion" as used herein refers to a state in which two materials, at least one biological in nature, are held together for an extended period of time by forces at the interface between them. In biological systems, bioadhesion can be classified into three types: (1) adhesion between two biological phases (e.g., wound healing); (2) adhesion of a biological phase to an artificial substrate; and (3) adhesion of an artificial material to a biological substrate. If adhesive attachment is to a mucus coat, the phenomenon is referred to as mucoadhesion. Shaikh, R. et al, "Mucoadhesive drug delivery systems," J. Pharm. Bioallied Sci. 3(1): 89-100 (2011). Polymers that adhere to biological surfaces can be divided into three broad categories: polymers that adhere through nonspecific, noncovalent interactions which are primarily electrostatic in nature; polymers possessing hydrophilic functional groups that hydrogen bond with similar groups on biological substrates; and polymers that bind to specific receptor sites on the cell or mucus surface. Exemplary polymers that bind to specific receptor sites on the cell or mucus surface include lectins (generally defined as proteins or glycoprotein complexes that are able to bind sugars selectively in a noncovalent manner, and thiolated polymers or thiomers, which are hydrophilic macromolecules exhibiting free thiol groups on the polymeric backbone Exemplary bioadhesive polymers include polycarbophil (polycyclic acid cross-linked with divinyl glycol, carbopol/carbomer (carboxy polymethylene), hydroxypropylmethyl cellulose HPMC (cellulose 2-hydroxypropylmethyl ether); hydroxyethyl cellulose; xanthan gum; guar gum; hydroxypropyl guar; chitosan; sodium aleginate; carrageenan; poly (hydroxyl butyrate), poly (e-caprolactone) and copolymers; and poly (ortho esters). See Roge, A. B., et al, "Bioadhesive Polymer: A Review," J. Pharmaceutical & Biomed. Sci. 5(25): (2011).

The term "biocompatible" as used herein refers to causing no clinically relevant tissue irritation, injury, toxic reaction, or immunological reaction to living tissue.

The term "biodegradable" as used herein refers to material that will break down actively or passively over time by simple chemical processes, by action of body enzymes or by other similar biological activity mechanisms.

The term "carrier" as used herein describes a material that does not cause significant irritation to an organism and does not abrogate the biological activity and properties of the compound of the composition of the described invention. Carriers must be of sufficiently high purity and of sufficiently low toxicity to render them suitable for administration to the mammal being treated. The carrier can be inert, or it can possess pharmaceutical benefits. The terms "excipient", "carrier", or "vehicle" are used interchangeably to refer to carrier materials suitable for formulation and administration of pharmaceutically acceptable compositions described herein. Carriers and vehicles useful herein include any such materials know in the art which are nontoxic and do not interact with other components.

The term "chemotherapeutic agent" or "cytotoxic agent" as used herein refers to agents useful in the treatment or control of a disease, e.g., cancer, or various forms of cancer.

The term "colorant" as used herein refers to a substance used to impart a color on a composition to improve the attractiveness of the composition and/or to enable easy product identification. Nonlimiting examples of colorants include oil-soluble dyes, oil dispersible dyes, water-soluble dyes, e.g. acid blue 3, acid blue 104, acid green 1, acid green 25, acid yellow 3, acid yellow 73 sodium salt, D&C green No. 5, 6, & 8, D&C yellow No. 7, 8, 10, & 11, D&C violet No. 2, FD&C blue No. 1 & 2, FD&C green No. 3, FD&C yellow No. 5 & 6, and mixtures thereof.

The term "compatible" as used herein refers to the components of a composition are capable of being combined with each other in a manner such that there is no interaction that would substantially reduce the efficacy of the composition under ordinary use conditions.

The term "component" as used herein refers to a constituent part, element or ingredient.

The terms "composition" and "formulation" are used interchangeably herein to refer to a product of the described invention that comprises all active and inert ingredients.

The term "condition" as used herein, refers to a variety of health states and is meant to include disorders or diseases caused by any underlying mechanism or disorder, injury, and the promotion of healthy tissues and organs.

The term "consequence" as used herein refers to an effect, result or outcome of something that occurred earlier.

The term "contact" and all its grammatical forms as used herein refers to a state or condition of touching or of immediate or local proximity.

The term "controlled release" is intended to refer to any drug-containing formulation in which the manner and profile of drug release from the formulation are controlled. This includes immediate as well as non-immediate release formulations, with non-immediate release formulations including, but not limited to, sustained release and delayed release formulations. The term "sustained release" (also referred to as "extended release") is used herein in its conventional sense to refer to a drug formulation that provides for gradual release of a drug over an extended period of time, and that preferably, although not necessarily, results in substantially constant levels of a drug over an extended time period. The term "delayed release" is used herein in its conventional sense to refer to a drug formulation in which there is a time delay between administration of the formulation and the release of the drug therefrom. "Delayed release" may or may not involve gradual release of drug over an extended period of time, and thus may or may not be "sustained release." The term "long-term" release, as used herein, means that the drug formulation is constructed and arranged to deliver therapeutic levels of the active ingredient for at least: 2 hours, 3 hours, 4 hours, hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, 48 hours, 49 hours, 50 hours, 51 hours, 52 hours, 53 hours, 54 hours, 55 hours, 56 hours, 57 hours, 58 hours, 59 hours, 60 hours, 61 hours, 62 hours, 63 hours, 64 hours, 65 hours, 66 hours, 67 hours, 68 hours, 69 hours, 70 hours, 71 hours, 72 hours, 73 hours, 74 hours, 75 hours, 76 hours, 77 hours, 78 hours, 79 hours, 80 hours, 81 hours, 82 hours, 83 hours, 84 hours, 85 hours, 86 hours, 87 hours, 88 hours, 89 hours, 90 hours, 91 hours, 92 hours, 93 hours, 94 hours, 95 hours, 96 hours, 97 hours, 98 hours, 99 hours, 100 hours, 101 hours, 102 hours, 103 hours, 104 hours, 105 hours, 106 hours, 107 hours, 108 hours, 109 hours, 110 hours, 111 hours, 112 hours, 113 hours, 114 hours, 115 hours, 116 hours, 117 hours, 118 hours, 119 hours, or 120 hours.

The term "copolymer" as used herein refers to those a polymer derived from more than one species of monomer. The term "polymer" refers to a large molecule, or macromolecule, composed of many repeated subunits. The term "monomer" refers to a molecule that may bind chemically to other molecules to form a polymer.

The term "derivative" as used herein means a compound that may be produced from another compound of similar structure in one or more steps. A "derivative" or "derivatives" of a compound retains at least a degree of the desired function of the compound. Accordingly, an alternate term for "derivative" may be "functional derivative." Derivatives can include chemical modifications, such as alkylation, acylation, carbamylation, iodination or any modification that derivatizes the compound. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formal groups. Free carboxyl groups can be derivatized to form salts, esters, amides, or hydrazides. Free hydroxyl groups can be derivatized to form O-acyl or O-alkyl derivatives. The imidazole nitrogen of histidine can be derivatized to form N-im-benzylhistidine. Also included as derivatives or analogs are those peptides that contain one or more naturally occurring amino acid derivative of the twenty standard amino acids, for example, 4-hydroxyproline, 5-hydroxylysine, 3-methyl-histidine, homoserine, ornithine or carboxyglutamiate, and can include amino acids that are not linked by peptide bonds. Such peptide derivatives can be incorporated during synthesis of a peptide, or a peptide can be modified by well-known chemical modification methods (see, e.g., Glazer et al., Chemical Modification of Proteins, Selected Methods and Analytical Procedures, Elsevier Biomedical Press, New York (1975)).

The term "demulcents" as used herein refers to protective agents employed primarily to alleviate irritation, particularly with respect to mucous membranes or abraded tissues. A number of chemical substances possess demulcent properties. Exemplary demulcents include alginates, mucilages, gums, dextrins, starches, certain sugars, and polymeric polyhydric glycols. Others include acacia, agar, benzoin, carbomer, gelatin, glycerin, hydroxyethyl cellulose, hydroxypropyl cellulose, hydroxypropyl methylcellulose, propylene glycol, sodium alginate, tragacanth, hydrogels and the like.

The term "disease" or "disorder" as used herein refers to an impairment of health or a condition of abnormal functioning.

The term "dispersion" as used herein, refers to a two-phase system, in which one phase is distributed as particles or droplets in the second, or continuous phase. In these systems, the dispersed phase frequently is referred to as the discontinuous or internal phase, and the continuous phase is called the external phase or dispersion medium. For example, in coarse dispersions, the particle size is 0.5 mm. In colloidal dispersions, size of the dispersed particle is in the range of approximately 1 nm to 0.5 mm. A molecular dispersion is a dispersion in which the dispersed phase consists of individual molecules; if the molecules are less than colloidal size, the result is a true solution.

The term "drug" as used herein refers to any substance which is intended for use in the diagnosis, cure, mitigation, treatment or prevention of disease or disorder, or to affect the structure or function of the body The term "emulsion" as used herein refers to a two-phase system prepared by combining two immiscible liquid carriers, one of which is disbursed uniformly throughout the other and consists of globules that have diameters equal to or greater than those of the largest colloidal particles. The globule size is critical and must be such that the system achieves maximum stability. Usually, separation of the two phases will occur unless a third substance, an emulsifying agent, is incorporated. Thus, a basic emulsion contains at least three components, the two immiscible liquid carriers and the emulsifying agent, as well as the active ingredient. Most emulsions incorporate an aqueous phase into a non-aqueous phase (or vice versa). However, it is possible to prepare emulsions that are basically non-aqueous, for example, anionic and cationic surfactants of the non-aqueous immiscible system glycerin and olive oil.

The term "film" as used herein refers to a thin skin or membrane.

The term "film forming agent" as used herein refers to substances that leave pliable, cohesive, and continuous coverings when applied to a surface.

The term "flavorant" as used herein refers to substances that impart a sensory impression of a substance to improve its taste or palatability. Flavors are volatile organic chemicals; most have simple, well-characterized structures with a single functional group (i.e., a chemically reactive subunit) and a low molecular weight. Flavors can be categorized as artificial flavors, spices, and natural flavors. The term "natural flavor" as used herein refers to the essential oil, oleoresin, essence or extractive, protein hydrolysate, distillate, or any product of roasting, heating or enzymolysis, which contains the flavoring constituents derived from a spice, fruit or fruit juice, vegetable or vegetable juice, edible yeast, herb, bark, bud, root, leaf or similar plant material, meat, seafood, poultry, eggs, dairy products, or fermentation products thereof, whose significant function is flavoring rather than nutritional. The term "spice" as used herein refers to any aromatic vegetable substance in the whole, broken or ground form, except for those substances which have been traditionally regarded as foods, such as onions, garlic and celery; whose significant function is one of seasoning rather than nutritional; that is true to name, and from which no portion of any volatile oil or other flavoring principle has been removed. The term "artificial flavor" or "artificial flavoring" as used herein refers to any substance, the function of which is to impart flavor, which is not derived from a spice, fruit or fruit juice, vegetable or vegetable juice, edible yeast, herb, bark, bud, root, leaf or similar plant material, meat, fish, poultry, eggs, dairy products, or fermentation products thereof. Nonlimiting examples of flavorants include citric acid, glycine, monosodium glutamate, fruit juices, and aromatic oils.

The term "folding endurance" as used herein refers to the number of folds (meaning bends over on itself so one part covers another and the return back to the starting position) a material can withstand before it breaks, e.g., at least 50 folds, at least 60 folds, at least 70 folds, at least 80 folds, at least 90 folds, at least 100 folds, at least 110 folds, at least 120 folds, at least 130 folds, at least 140 folds, at least 150 folds, at least 160 folds, at least 170 folds, at least 180 folds, at least 190 folds, at least 200 folds, at least 210 folds, at least 220 folds, at least 230 folds, at least 240 folds, at least 250 folds, at least 260 folds, at least 270 folds, at least 280 folds, at least 290 folds, at least 300 folds, at least 310 folds, at least 320 folds, at least 330 folds, at least 340 folds, at least 350 folds, at least 360 folds, at least 370 folds, at least 380 folds, at least 390 folds, at least 400 folds at least 410 folds, at least 420 folds, at least 430 folds, at least 440 folds, at least 450 folds, at least 460 folds, at least 470 folds, at least 480 folds, at least 490 folds, or at least 500 folds.

The term "fragrance" as used herein refers to a substance that imparts a pleasant scent. Nonlimiting examples include aromatic oils (i.e., peppermint or lemon oil), herbs, spices, and distilled fractions thereof.

The term "hydroalcoholic solvent" as used herein refers to a solvent containing both water and an alcohol.

The term "hydrate" as used herein refers to a compound formed by the addition of water or its elements to another molecule. The water usually can split off by heating, yielding the anhydrous compound.

The term "hydrogel" as used herein refers to a substance resulting in a solid, semisolid, pseudoplastic, or plastic structure containing a necessary aqueous component to produce a gelatinous or jelly-like mass.

The term "hydrophilic" as used herein refers to a material or substance having an affinity for polar substances, such as water.

The term "immunomodulatory agent" as used herein refer(s) to an agent capable of augmenting or diminishing immune responses.

The term "immunosuppressant" as used herein refers to a substance used to reduce the immune response in organ transplantation and autoimmune disease.

The term "impregnate" as used herein in its various grammatical forms refers to causing to be infused or permeated throughout, or to fill interstices with a substance.

The term "keratolytic agent" as used herein refers to substances that thin or soften the skin on and around skin lesions. Exemplary keratolytic agents include urea, lactic acid, allantoin, benzoyl peroxide, salicyclic acid, sulfur, tretinoin, fluorouracil, trichloroacetic acid, and glycolic acid.

The term "labile" as used herein refers to that which is subject to increased degradation.

The term "lipophilic" as used herein refers to preferring or possessing an affinity for a non-polar environment compared to a polar or aqueous environment.

The term "local anesthetic" as used herein refers to any drug that provides local numbness or analgesia or any drug that provides a regional blockage of nociceptive pathways (afferent and/or efferent). The meaning of "local anesthetic" as used herein also encompasses drugs not traditionally associated with local anesthetic properties but which have a local anesthetic effect, for example, non-narcotic analgesics, such as, acetylsalicylic acid, ketoprofen, piroxicam, diclofenac, indomethacin, ketorolac, rofecoxib, and celecoxib, and pharmaceutically acceptable salts thereof, or mixtures thereof.

The phrase "localized administration", as used herein, refers to administration of a therapeutic agent in a particular location in the body.

The phrase "localized pharmacologic effect", as used herein, refers to a pharmacologic effect limited to a certain location, i.e. in proximity to a certain location, place, area or site. The phrase "predominantly localized pharmacologic effect", as used herein, refers to a pharmacologic effect of a drug limited to a certain location by at least 1 to 3 orders of magnitude, which is achieved by a localized administration as compared to a systemic administration.

The term "matrix" as used herein refers to a three dimensional network of fibers that contains voids (or "pores") where the woven fibers intersect. The structural parameters of the pores, including the pore size, porosity, pore interconnectivity/tortuosity and surface area, affect how substances (e.g., fluid, solutes) move in and out of the matrix.

The term "maximum tolerated dose" as used herein refers to the highest dose of a drug that does not produce unacceptable toxicity.

The term "mineral nutrient" or "essential mineral" are used interchangeably to refer to an inorganic substance required by a cell in small amounts for a variety of functions, e.g., as components of enzyme systems. The term "salt" as used herein refers to a compound that results from the replacement of one or more hydrogen atoms of an acid by metal atoms or electropositive radicals. Exemplary minerals and salts include, for example, sodium, potassium, calcium, magnesium, copper, manganese, molybdenum, selenium, silicon, iron, zinc, vanadium, boron, cobalt, iodine, chromium and tin. Minerals or salts can be provided as organic (organic acids) or inorganic salts (e.g., chlorides, sulfates, phosphates or nitrates). In a non-limiting example, a selenium salt is sodium selenite. Amounts or concentrations of minerals or salts will depend upon the particular mineral or salt.

The terms "minimum effective concentration," "minimum effective dose," or "MEC" are used interchangeably to refer to the minimum concentration of a drug required to produce a desired pharmacological effect in most patients.

The term "nicotinic cholinergic receptor agonist" as used herein refers to a drug that mimics the stimulatory action of acetylcholine and other nicotine-like agents by binding at nicotinic acetylcholine receptors, which activates the receptors. Nicotinic cholinergic receptors are ligand-gated ion channels that form pores in the plasma membrane, mediating fast signal transmission at synapses. They are involved in a wide range of physiological processes, and can be either neuronal or muscle type. Nicotine use is powerfully addictive. Since nicotine is structurally similar to the neurotransmitter acetylcholine, it can activate these cholinergic receptors. Unlike acetylcholine, nicotine enters the brain and disrupts its normal functioning. Regular intake of nicotine leads to a change in the number of cholinergic receptors and to changes in their sensitivity to nicotine, which can lead to the development of nicotine tolerance. Nicotine in inhaled tobacco smoke or in smokeless tobacco applied to buccal or nasal mucosa enters the circulation within seconds, causing an increase in heart rate, ventricular stroke volume, and myocardial oxygen consumption, as well as euphoria, heightened alertness, and a sense of relaxation. Withdrawal from nicotine causes restlessness, irritability, anxiety, difficulty concentrating and craving for nicotine.

The term "non-steroidal anti-inflammatory agents" as used herein refers to a large group of anti-inflammatory agents that are aspirin-like in their action.

The term "non-cellulosic copolymer" as used herein refers to a copolymer not containing or derived from cellulose.

The terms "penetration enhancer" and "permeation enhancer" are used interchangeably to refer to natural or synthetic molecules that facilitate the transport of co-administered active agents across biological membranes.

The term "pH modifier" as used herein refers to a substance used to achieve desired pH control in a formulation. Exemplary pH modifiers include acids (e.g., acetic acid, adipic acid, carbonic acid, citric acid, fumaric acid, phosphoric acid, sorbic acid, succinic acid, tartaric acid, basic pH modifiers (e.g., magnesium oxide, tribasic potassium phosphate, Eudragit® E, and pharmaceutically acceptable salts thereof.

The term "pharmaceutical composition" is used herein to refer to a composition that is employed to prevent, reduce in intensity, cure or otherwise treat a target condition or disease.

As used herein the phrase "pharmaceutically acceptable carrier" refers to any substantially non-toxic carrier useable for formulation and administration of the composition of the described invention in which the product of the described invention will remain stable and bioavailable. The pharmaceutically acceptable carrier must be of sufficiently high purity and of sufficiently low toxicity to render it suitable for administration to the mammal being treated. It further should maintain the stability and bioavailability of an active agent. The pharmaceutically acceptable carrier can be liquid or solid and is selected, with the planned manner of administration in mind, to provide for the desired bulk, consistency, etc., when combined with an active agent and other components of a given composition.

The term "pharmaceutically acceptable salt" as used herein refers to those salts which are, within the scope of sound medical judgment, suitable for use in contact with the tissues of humans and lower animals without undue toxicity, irritation, allergic response and the like and are commensurate with a reasonable benefit/risk ratio. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts may be prepared as alkaline metal or alkaline earth salts, such as sodium, potassium or calcium salts of the carboxylic acid group. For example, P. H. Stahl, et al. describe pharmaceutically acceptable salts in detail in "Handbook of Pharmaceutical Salts: Properties, Selection, and Use" (Wiley VCH, Zurich, Switzerland: 2002). The salts may be prepared in situ during the final isolation and purification of the compounds described within the present invention or separately by reacting a free base function with a suitable organic acid. Representative acid addition salts include, but are not limited to, acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, fumarate, hydrochloride, hydrobromide, hydroiodide, 2-hydroxyethansulfonate(isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups may be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid. Basic addition salts may be prepared in situ during the final isolation and purification of compounds described within the invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like. Pharmaceutically acceptable salts also may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium or magnesium) salts of carboxylic acids may also be made.

The term "pharmacologic effect", as used herein, refers to a result or consequence of exposure to an active agent.

The term "plasticizer" as used herein refers to a material that, when added to a polymer, imparts an increase in flexibility, workability, and other properties to the finished product.

The term "potency" as used herein refers to efficacy, effectiveness, or strength of a drug. The potency of a drug is the reciprocal of dose, and has the units of persons/unit weight of drug or body weight/unit weight of drug. Relative potency compares the relative activity of drugs in a series relative to some prototypic member of the series. "Efficacy" connotes the property of a drug to achieve the desired response, and maximum efficacy denotes the maximum achievable effect.

The term "preservative" as used herein refers to a substance that prevents or inhibits microbial growth. Nonlimiting examples include quaternarium ammonium compounds (e.g., benzalkonium chloride, chlorobutanol, parabens (e.g., methylparaben, propylparaben), phenylmercuric acetate/nitrate, thimerosal, acids (e.g. sorbic acid, benzoic acid), alcohols (e.g. benzyl alcohol), organic sulfur compounds (e.g. 3-isothiazolone compounds, sodium pyrithione), halogenated compounds (e.g. chlorhexidine, chlorobutanol), cyclic organic nitrogen compounds (e.g. imidazolidinedione compounds, polymethoxy bicyclic oxazolidine), low molecular weight aldehydes (e.g. formaldehyde, glutaraldehyde), and mixtures thereof.

The term "phase transfer catalyst" as used herein refers to a substance that facilitates the migration of a reactant from one phase into another phase where reaction occurs. Nonlimiting examples include quaternary ammonium salts and organic phosphonium salts.

The term "reduced" or "to reduce" as used herein refers to a diminution, a decrease, an attenuation or abatement of the degree, intensity, extent, size, amount, density or number.

The term "release" and its various grammatical forms, refers to dissolution of an active drug component and diffusion of the dissolved or solubilized species by a combination of the following processes: (1) hydration of a matrix, (2) diffusion of a solution into the matrix; (3) dissolution of the drug; and (4) diffusion of the dissolved drug out of the matrix.

The term "retinoid" as used herein refers to a class of chemical compounds that are forms of Vitamin A, or are chemically related to it.

The term "similar" is used interchangeably with the terms analogous, comparable, or resembling, meaning having traits or characteristics in common.

The term "skin disorder" as used herein, refers to any disorder or abnormality of the skin. Non-limiting examples of skin disorders include pruritus, atopic dermatitis, psoriasis, acne, skin infections and infestations, skin neoplasms, and alopecia.

The terms "soluble" and "solubility" refer to the property of being susceptible to being dissolved in a specified fluid (solvent). The term "insoluble" refers to the property of a material that has minimal or limited solubility in a specified solvent. In a solution, the molecules of the solute (or dissolved substance) are uniformly distributed among those of the solvent. A "suspension" is a dispersion (mixture) in which a finely-divided species is combined with another species, with the former being so finely divided and mixed that it doesn't rapidly settle out. In everyday life, the most common suspensions are those of solids in liquid.

The terms "solubility enhancer" or "solubilizing agent" are used interchangeably to refer to any chemical and/or biological agent able to improve the solubility of an agent in a solvent. Exemplary solubility enhancers include povidone, cholesterol, cyclodextrins, and polyethylene glycols.

Povidone (2-pyrrolidinone, polyvinylpyrrolidone; PVP), is a synthetic polymer consisting of linear 1-vinyl-2-pyrrolidinone groups; it is produced commercially as a series of products having mean molecular weights ranging from about 10,000 to about 700,000. The viscosity of solutions containing 10% or less PVP is essentially the same as that of water; solutions more concentrated than 10% become more viscous, depending on the concentration and molecular weight of the polymer used.

Cholesterol can be used to enhance incorporation and emulsification of medicinal products in oils or fats.

Cyclodextrins (CDs) are a family of cyclic oligosaccharides containing α-D-glucose units joined with glycosidic (ether) linkages. Commercially available cyclodextrins include α-cyclodextrin (cyclohexamylose, consisting of 6 glucose units), β-cyclodextrin (cycloheptaamylose, consisting of 7 glucose units), and γ-cyclodextrin (cyclooctaamylose, consisting of 8 glucose units). The interior of the cavity, which can act as host for a wide variety of lipophilic compounds, is lined with these glycosidic bonds and, therefore, is relatively nonpolar (relative to water), whereas the exterior of the molecule is quite polar because of the large number of hydroxyl groups, which can be derivatized. Examples of such derivatives of β cyclodextrin are dimethylated and hydroxypropylated β-cyclodextrin, DM-β-CD and HP-β-CD. These derivatized cyclodextrins have a higher solubility as well as a more hydrophobic cavity compared to nonderivatized β-cyclodextrin. Cyclodextrins DM-β-CD has been reported as having an absorption enhancing effect. (See, e.g., Hovgaard, L and Brondsted, H., "Drug delivery studies in Caco-2 monolayers. IV. Absorption enhancer effects of cyclodextrins," Pharmaceutical Res. 12(9): 1328-32 ((1995)). Schipper, N G M et al, "Nasal administration of an ACTH (4-9) peptide analogue with dimethyl-β-cyclodextrin as an absorption enhancer: pharmacokinetics and dynamics," Br. J. Pharmacol. 110: 1335-40 (1993)).

Polyethylene glycols possess a wide range of solubilities and compatibilities, which make them useful in pharmaceutical preparations.

Exemplary solubility enhancers include surfactants, which act as solubilizing agents by forming micelles. The HLB system is used to describe the characteristics of a surfactant. It is an arbitrary scale to which HLB values are experimentally determined and assigned. If the HLB value is low, the number of hydrophilic groups on the surfactant is small, which means it is more lipophilic (oil soluble) than hydrophilic (water soluble). Conversely, if the HLB value is high, there are a large number of hydrophilic groups on the surfactant, which makes it more hydrophilic (water soluble) than oil soluble. An HLB value of 10 or higher means that the agent is primarily hydrophilic.

Antifoaming agents (HLB 1-3) dissipate foam by destabilizing the air:liquid interface, which allows the liquid to drain away from the air pocket (e.g., alcohol, ether, castor oil, and some surfactants).

Emulsifying agents (HLB 3-6 (w/o) and 8-18 (o/w) are surfactants that reduce the interfacial tension between oil and water, thereby minimizing the surface energy through formation of globules; examples include, e.g., glyceryl monostearate, methylcellulose, sodium lauryl sulfate, sodium oleate, sorbitan monopalmitate, sorbitan monostearate, sorbitan tristrearate, tragacanth, triethanolamine oleate, polyethylene sorbitan monolaurate; poloxamer (Pluronic F-68)).

The term "solvate" as used herein refers to a complex formed by the attachment of solvent molecules to that of a solute.

The term "solvent" refers to a substance capable of dissolving another substance (termed a "solute") to form a uniformly dispersed mixture (solution).

The term "steroidal anti-inflammatory agent", as used herein, refer to any one of numerous anti-inflammatory compounds containing a 17-carbon 4-ring system and includes the sterols, various hormones (as anabolic steroids), and glycosides.

The terms "subject" or "individual" or "patient" are used interchangeably to refer to a member of an animal species of mammalian origin, including humans.

The phrase "subject in need thereof" as used herein refers to a subject that (i) will be administered a topical film-forming composition of the described invention; (ii) is applying the topical film-forming composition of the described invention; or (iii) has applied the topical film-forming composition of the described invention, unless the context and usage of the phrase indicates otherwise.

The term "susceptible" as used herein refers to being at risk for.

The term "symptom" as used herein refers to a phenomenon that arises from and accompanies a particular disease or disorder and serves as an indication of it.

The term "syndrome," as used herein, refers to a pattern of symptoms indicative of some disease or condition.

The term "synergistic effect", as used herein, refers to a combined effect of two chemicals, which is greater than the sum of the effects of each agent given alone.

The phrase "systemic administration", as used herein, refers to administration of a therapeutic agent with a pharmacologic effect on the entire body. Systemic administration includes enteral administration (e.g. oral) through the gastrointestinal tract and parenteral administration (e.g. intravenous, intramuscular, etc.) outside the gastrointestinal tract.

The term "tensile strength" as used herein refers to the force needed to pull a material apart. Tensile strength is measured in force/cross-sectional area. The amount of deformation a material will undergo during a tensile test is strain, which is calculated as the change in the length of a portion of the sample divided by the original length.

The term "therapeutic agent" as used herein refers to a drug, molecule, composition or other substance that provides a therapeutic effect. The term "active" as used herein refers to the ingredient, component or constituent of the compositions of the present invention responsible for the intended therapeutic effect. The terms "therapeutic agent" and "active agent" are used interchangeably.

The terms "therapeutic amount", "therapeutic effective amount" or an "amount effective" of one or more of the therapeutic agents is an amount that is sufficient to provide the intended benefit of treatment. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen may be planned which does not cause substantial toxicity and yet is effective to treat the particular subject. It is preferred generally that a maximum dose be used, that is, the highest safe dose according to some medical judgment. However, dosage levels are based on a variety of factors, including the type of injury, the age, weight, sex, medical condition of the patient, the severity of the condition, the route of administration, and the particular therapeutic agent employed. Thus the dosage regimen may vary widely, but can be determined routinely by a surgeon using standard methods. "Dose" and "dosage" are used interchangeably herein.

The term "therapeutic component" as used herein refers to a therapeutically effective dosage (i.e., dose and frequency of administration) that eliminates, reduces, or prevents the progression of a particular disease manifestation in a percentage of a population. An example of a commonly used therapeutic component is the ED50 which describes the dose in a particular dosage that is therapeutically effective for a particular disease manifestation in 50% of a population.

The term "therapeutic effect" as used herein refers to a consequence of treatment, the results of which are judged to be desirable and beneficial. A therapeutic effect may include, directly or indirectly, the arrest, reduction, or elimination of a disease manifestation. A therapeutic effect may also include, directly or indirectly, the arrest reduction or elimination of the progression of a disease manifestation.

The terms "topically", "topical administration" and "topically applying" are used interchangeably to refer to delivering a pharmaceutical composition of the described invention onto one or more surfaces of a tissue or cell, including epithelial surfaces. The term "topical" refers to administration of a pharmaceutical composition at, or immediately beneath, the point of application. The composition may be applied by pouring, dropping, or spraying, if a liquid; rubbing on, if an ointment, lotion, cream, gel, or the like; dusting, if a powder; spraying, if a liquid or aerosol composition; or by any other appropriate means. Topical administration generally provides a local rather than a systemic effect.

The term "treat" or "treating" includes abrogating, substantially inhibiting, slowing or reversing the progression of a disease, condition or disorder, substantially ameliorating clinical or esthetical symptoms of a condition, substantially preventing the appearance of clinical or esthetical symptoms of a disease, condition, or disorder, and protecting from harmful or annoying symptoms. The term "treat" or "treating" as used herein further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and (e) limiting recurrence of symptoms in patients that were previously symptomatic for the disorder(s).

The term "viscosity" as used herein refers to the property of a fluid that resists the force tending to cause the fluid to flow. Viscosity is a measure of the fluid's resistance to flow. The resistance is caused by intermolecular friction exerted when layers of fluids attempt to slide by one another. Viscosity can be of two types: dynamic (or absolute) viscosity and kinematic viscosity. Absolute viscosity or the coefficient of absolute viscosity is a measure of the internal resistance. Dynamic (or absolute) viscosity is the tangential force per unit area required to move one horizontal plane with respect to the other at unit velocity when maintained a unit distance apart by the fluid. Dynamic viscosity is usually denoted in poise (P) or centipoise (cP), wherein 1 poise=1 g/cm2, and 1 cP=0.01 P. Kinematic viscosity is the ratio of absolute or dynamic viscosity to density. Kinematic viscosity is usually denoted in Stoke (St) or Centistokes (cSt), wherein 1 St=10-4 m2/s, and 1 cSt=0.01 St.

The terms "viscosity modifier", "thickening agent" or "thickener" are used interchangeably herein to refer to agents that make a composition of the described invention dense or viscous in consistency. Physical properties of importance include, without limitation, solubility in different solvents, pH range of maximum viscosity, and rheologic characterization. Exemplary viscosity modifiers include, without limitation, acacia, agar, alginic acid, attapulgite, bentonite, carbomer 910, 934, 934P, 940, 941, 971P, 974P, and 1342 NF, carboxymethylcellulose, carrageenan, microcrystalline cellulose, dextrin, gelatin, guar gum, ghatty gum, hydroxyethyl cellulose, hydroxypropylcellulose, hydroxypropylmethylcellulose, magnesium aluminum silicate, methylcellulose, pectin, poloxamer, polyethylene oxide, polyvinyl alcohol, povidone, propylene glycol alginate, silicon dioxide, sodium alginate, tragacanth, and xanthan gum.

The term "vitamin" as used herein, refers to any of various organic substances essential in minute quantities to the nutrition of most animals act especially as coenzymes and precursors of coenzymes in the regulation of metabolic processes.

The term "wrinkle" as used herein refers to a furrow, fold or crease in the skin.

Composition

According to one aspect, the described invention provides a topical bioadhesive film-forming pharmaceutical composition comprising: (a) a therapeutic amount of an active agent; and (b) one or more excipients selected from the group consisting of a non-cellulosic polymer or copolymer, a film forming agent, a plasticizer, a permeation enhancer, an antioxidant, an antimicrobial agent, a preservative, a solubilizer, a phase transfer catalyst, a viscosity modifier, a mineral nutrient, a solvent, a colorant and a fragrance.

Exemplary active agents include, without limitation, analgesic agents, anesthetic agents; anti-acne agents; antibiotic agents; anti-fungal agents; anti-histamines, anti-inflammatory agents (steroidal and non-steroidal); anti-oxidant agents; a nicotinic cholinergic receptor agonist, anti-protozoal agents; anti-pruritic agents; anti-viral agents; chemotherapeutic agents, immunomodulatory agents, keratolytic agents, anti-aging agents, retinoids, and wound healing agents, among others.

According to some embodiments, the active agent can be an analgesic. Exemplary analgesics include non-steroidal anti-inflammatory drugs (NSAIDS), e.g., paracetamol (acetaminophen), ibuprofen, naproxen, and, COX-2 inhibitors, opioids, flupirtine, and specific agents including, but not limited to tricyclic antidepressants, such as amitriptyline, nefopam, and anticonvulsants, including carbamazepine, gabapentin, and pregabalin.

Non-limiting examples of anesthetic agents include lidocaine, bupivacaine, chlorprocaine, dibucaine, etidocaine, mepivacaine, tetracaine, dyclonine, hexylcaine, procaine, cocaine, ketamine, pramoxine, and phenol.

Exemplary anti-acne agents include sulfur, glycolic, pyruvic acid, resorcinol, N-acetylcysteine, picolinic acid, picolinic acid derivatives, picolinic acid analogs, benzoyl peroxide, retinoids such as retinoic acid and its derivatives (e.g., cis and trans, esters), and antibiotic agents in the tetracycline-class of antibiotics (e.g., Minocycline).

Exemplary classes of antibiotic agents include, without limitation, β-lactams; cephalosporins, fluoroquinolones, aminoglycosides, minobactams, catbapenems, and macrolides. Others include, without limitation, vancomycin, rifampin, doxycycline, linezolid, tetracyclines, trimethoprim/sulfamethoxacole, and other biotechnology derived glycolated peptides, and monoclonal antibodies.

Exemplary beta-lactam antibiotic agents include penicillin g, penicillin-vk, methicillin, nafcillin, oxacillin, cloxacillin; dicloxacillin, amoxicillin; ticarcillin; carbenicillin; mezlocillin; azlocillin; and piperacillin. exemplary cephalosporins include cephalothin, cefazolin, cephaprin, cephalexin, cefaclor, cefotetan, ceftriaxone, cefpirome, cefepime, cefoxitin; cefuroxime; cefonicid, cefmetazole; cefotetan; cefprozil; cefetamet; cefoperazone; cefotaxime; ceftizoxime; ceftriaxone; ceftazidime; cefixime; cefpodoxime; and cefsulodin. exemplary fluoroquinolones include nalidixic acid, ciprofloxacin, levofloxacin, moxifloxacin, ofloxacin; enoxacin; lomefloxacin; cinoxacin and norfloxacin. Exemplary aminoglycosides include amikacin, gentamicin, kanamycin, neomycin, and tobramycin. Exemplary monobactams include aztreonam, tigemonam, nocardicin a, and tabtoxin. Exemplary carbapenams include aztreonam, ertapenem, imipenem, and meropenem. Exemplary macrolides include azithromycin, clarithromycin, dirithromycin, erythromycin, erythromycin estolate; erythromycin ethyl succinate; erythromycin glucoheptonate; erythromycin lactobionate; erythromycin stearate and clindamycin. Exemplary tetracyclines include tetracycline, chloretracycline, oxyetracycline, demeclocycline, lymecycline, meclocycline, methacycline, minocycline, and rolitetracycline.

Exemplary anti-fungal agents include amphotericin b, candicidin, dermostatin, filipin, fungichromin, hachimycin, hamycin, lucensomycin, mepartricin, natamycin, nystatin, pecilocin, perimycin, azaserine, griseofulvin, oligomycins, neomycin, pyrrolnitrin, siccanin, tubercidin, viridin, butenafine, naftifine, terbinafine, bifonazole, butoconazole, chlordantoin, chlormidazole, cloconazole, clotrimazole, econazole, enilconazole, fenticonazole, flutrimazole, isoconazole, ketoconazole, lanoconazole, miconazole, omoconazole, oxiconazole, sertaconazole, sulconazole, tioconazole, tolciclate, tolindate, tolnaftate, fluconazole, itraconazole, saperconazole, terconazole, acrisorcin, amorolfine, biphenamine, bromosalicylchloranilide, buclosamide, calcium propionate, chlorphenesin, ciclopirox, cloxyquin, coparaffinate, diamthazole, exalamide, flucytosine, halethazole, hexetidine, loflucarban, nifuratel, potassium iodide, propionic acid, pyrithione, salicylanilide, sodium propionate, sulbentine, tenonitrozole, triacetin, ujothion, undecylenic acid, and zinc propionate.

An exemplary nicotinic cholinergic receptor agonist is nicotine. Nicotine, an alkaloid found in certain plants, is an oily liquid miscible with water in its base form. Nitrogenous forms of nicotine form salts with acids that are soluble in water. According to some embodiments the nicotine is in a nicotine base form. According to some embodiments, the nicotine is in a nicotine salt form.

Exemplary anti-protozoal agents include pyrimethamine (Daraprim®) sulfadiazine, and leucovorin.

Exemplary antipruritic agents include hydroxyzine, methdilazine, and trimeprazine.

Exemplary anti-viral agents include acyclovir, cidofovir, cytarabine, dideoxyadenosine, didanosine, edoxudine, famciclovir, floxuridine, ganciclovir, idoxuridine, inosine pranobex, lamivudine, madu, penciclovir, sorivudine, stavudine, trifluridine, valacyclovir, vidarabine, zaicitabine, acemannan, acetylleucine, amantadine, amidinomycin, delavirdine, foscarnet, indinavir, interferons (e.g., ifn-alpha), kethoxal, lysozyme, methisazone, moroxydine, nevirapine, podophyllotoxin, ribavirin, rimantadine, ritonavir, saquinavir, stailimycin, statolon, tromantadine, zidovudine (AZT) and xenazoic acid.

According to some embodiments, an immunomodulatory agent is an immunosuppressant. Exemplary immunosuppressants include glucocorticoids, calcineurin inhibitors, and antiproliferative/antimetabolic agents. Non-limiting examples of glucocorticoids include prednisone, prednisolone, methylprednisilone, dexamethasone, and hydrocortisone. Non-limiting examples of calcineurin inhibitors include cyclosporine and tacrolimus. Non-limiting examples of antiproliferative/antimetabolic agents include rapamycin, azathioprine, and mycophenolate mofetil.

Exemplary local anesthetics include, ambucaine, amolanone, amylcaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethisoquin, dimethocaine, diperodon, dyclonine, ecogonidine, ecogonine, euprocin, fenalcomine, formocaine, hexylcaine, hydroxyteracaine, isobutyl p-aminobenzoate, leucinocaine, levoxadrol, lidocaine, mepivacaine, meprylcaine, metabutoxycaine, methyl chloride, myrtecaine, naepaine, octacaine, orthocaine, oxethazaine, parenthoxycaine, phenacaine, phenol, piperocaine, piridocaine, polidocanol, pramoxine, prilocaine, procaine, propanocaine, proparacaine, propipocaine, propoxycaine, pseudococaine, pyrrocaine, ropivacaine, salicyl alcohol, tetracaine, tolycaine, trimecaine, zolamine, or a pharmaceutically acceptable salt thereof, or a mixture thereof. Amide type local anesthetics are characterized by an amide functionality, while ester type local anesthetics contain an ester functionality. Exemplary amide type local anesthetics include lidocaine, bupivacaine, prilocaine, mepivacaine, etidocaine, ropivacaine, dibucaine, and mixtures thereof. Exemplary ester type local anesthetics include tetracaine, procaine, benzocaine, chloroprocaine, their pharmaceutically acceptable salt, or a mixture thereof.

Exemplary chemotherapeutic agents include, without limitation, temozolomide, busulfan, ifosamide, melphalan, carmustine, lomustine, mesna, 5-fluorouracil, capecitabine, gemcitabine, floxuridine, decitabine, mercaptopurine, pemetrexed disodium, methotrexate, vincristine, vinblastine, vinorelbine tartrate, paclitaxel, docetaxel, ixabepilone, daunorubicin, epirubicin, doxorubicin, idarubicin, amrubicin, pirarubicin, mitoxantrone, etoposide, etoposide phosphate, teniposide, mitomycin C, actinomycin D, colchicine, topotecan, irinotecan, gemcitabine cyclosporin, verapamil, valspodor, probenecid, biricodar, terfenadine, quinidine, and pervilleine A.

Non-limiting examples of non-steroidal anti-inflammatory include, ibuprofen (Advil®), naproxen sodium (Aleve®), and acetaminophen (Tylenol®), oxicams, such as piroxicam, isoxicam, tenoxicam, sudoxicam, and CP-14, 304; disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents also may be employed, as well as the dermatologically acceptable salts and esters of these agents. For example, etofenamate, a flufenamic acid derivative, can be used for topical application.

Non-limiting examples of steroidal anti-inflammatory agents include corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflucortolone valerate, fluadrenolone, fluclorolone acetonide, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflorosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

Non-limiting examples of vitamins and nutrients usable in context of the present invention include vitamin A and its analogs and derivatives: retinol, retinal, retinyl palmitate, retinoic acid, tretinoin, iso-tretinoin (known collectively as retinoids), vitamin E (tocopherol and its derivatives), vitamin C (L-ascorbic acid and its esters and other derivatives), vitamin B3 (niacinamide and its derivatives), alpha hydroxy acids (such as glycolic acid, lactic acid, tartaric acid, malic acid, citric acid, etc.) and beta hydroxy acids (such as salicylic acid and the like).

Non-limiting examples of minerals and salts include, for example, sodium, potassium, calcium, magnesium, copper, manganese, molybdenum, selenium, silicon, iron, zinc, vanadium, boron, cobalt, iodine, chromium and tin. Minerals or salts can be provided as organic (organic acids) or inorganic salts (e.g., chlorides, sulfates, phosphates or nitrates). In a non-limiting example, a selenium salt is sodium selenite. Amounts or concentrations of minerals or salts will depend upon the particular mineral or salt.

Nonlimiting examples of retinoids include retinol, retinal, tretinoin, isotretinoin, alitretinoin, etretinate, acitretin, tazarotene, bexarotene, and adapalene.

According to some embodiments, the composition is an aseptic composition. According to some embodiments, the composition is a wound healing composition.

According to some embodiments, film formation occurs at room temperature. According to some embodiments, because the film is pliant, it adheres and conforms to surfaces of the skin. According to some embodiments, the film resists breaking under tension, i.e., has tensile strength. According to some embodiments, the film may be of any order release kinetics, including zero order release, first order release, second order release, delayed release, sustained release, immediate release, etc., and any combination thereof. The film-forming composition may further include any of those materials routinely used in the art of pharmacy and medicine, including, but not limited to, erodible, non-erodible, biodegradable, or nonbiodegradable material or combinations thereof. According to some embodiments, the film may be of virtually any shape. According to some embodiments, the film, once formed is removable without leaving a substantial residue.

According to some embodiments, the film comprises a matrix. According to some embodiments, the active agent releases from the film by diffusion according to Ficke's law. Accordingly, thickness of the film is not a consideration.

According to some embodiments, the release is a controlled release. According to some embodiments, the release is a delayed release. According to some embodiments, the release is a sustained release.

According to some embodiments, the composition is characterized by controlled release of locally sustained levels of a minimum effective concentration (MEC) of the active agent. According to some embodiments, the composition is pliant (meaning having a quality or tendency to bend that does not require force or pressure from the outside.

The intensity of effect of a drug (y-axis) can be plotted as a function of the dose of drug administered (X-axis). Goodman & Gilman's The Pharmacological Basis of Therapeutics, Ed. Joel G. Hardman, Lee E. Limbird, Eds., $10^{th}$ Ed., McGraw Hill, New York (2001), p. 25, 50). These plots are referred to as dose-effect curves. Such a curve can be resolved into simpler curves for each of its components. These concentration-effect relationships can be viewed as having four characteristic variables: potency, slope, maximal efficacy, and individual variation.

The location of the dose-effect curve along the concentration axis is an expression of the potency of a drug. Id. If the drug is to be administered by transdermal absorption, a highly potent drug is required, since the capacity of the skin to absorb drugs is limited.

According to some embodiments, potency of the active agent in the claimed composition is maintained within a range of from 90% to 250%, i.e., at least: 90%, 91%, 92%, 93%, 94%, 95%, 96%, 97%, 98%, 99% 100%, 110%, 120%, 130%, 140%, 150%, 160%, 170%, 180%, 190%, 200%, 210%, 220%, 230%, 240%, or 250%.

The slope of the dose-effect curve reflects the mechanism of action of a drug. The steepness of the curve dictates the range of doses useful for achieving a clinical effect.

Maximal or clinical efficacy refers to the maximal effect that can be produced by a drug. Maximal efficacy is determined principally by the properties of the drug and its receptor-effector system and is reflected in the plateau of the curve. In clinical use, a drug's dosage may be limited by undesired effects.

Biological variability. An effect of varying intensity may occur in different individuals at a specified concentration or a drug. It follows that a range of concentrations may be required to produce an effect of specified intensity in all subjects.

Lastly, different individuals may vary in the magnitude of their response to the same concentration of a drug when the appropriate correction has been made for differences in potency, maximal efficacy and slope.

The duration of a drug's action is determined by the time period over which concentrations exceed the MEC. Following administration of a dose of drug, its effects usually show a characteristic temporal pattern. A plot of drug effect vs. time illustrates the temporal characteristics of drug effect and its relationship to the therapeutic window. A lag period is present before the drug concentration exceeds the minimum effective concentration (MEC) for the desired effect. Following onset of the response, the intensity of the effect increases as the drug continues to be absorbed and distributed. This reaches a peak, after which drug elimination results in a decline in the effect's intensity that disappears when the drug concentration falls back below the MEC. The therapeutic window reflects a concentration range that provides efficacy without unacceptable toxicity. Accordingly another dose of drug should be given to maintain concentrations within the therapeutic window.

According to some embodiments, the concentration of the active agent is at least 1% w/w of the composition, at least 2% w/w of the composition, at least 3% w/w of the composition, at least 4% w/w of the composition, at least 5% w/w of the composition, at least 6% w/w of the composition, at least 7% w/w of the composition, at least 8% w/w of the composition, at least 9% w/w of the composition, at least 10% w/w of the composition; at least 11% w/w of the composition; at least 12% w/w of the composition; at least 13% w/w of the composition; at least 14% w/w of the composition; at least 15% w/w of the composition; at least 16% w/w of the composition; at least 17% w/w of the composition; at least 18% w/w of the composition; at least 19% w/w of the composition; at least 20% w/w of the composition, at least 30% w/w of the composition, at least 40% w/w of the composition, at least 50% w/w of the composition, or at least 60% w/w of the composition. According to some embodiments, the concentration of the active agent is from about 1% to about 10% w/w of the composition, i.e., at least 1%, at least 2%, at least 3%, at least 4%, at least 5%, at least 6%, at least 7%, at least 8%, at least 9%, or at least 10% w/w of the composition.

According to some embodiments, the content of the active agent retained on skin and its permeation/flux into the skin can be measured as a function of time. According to some embodiments, flux is determined using one of many available artificial membranes (e.g., Cuprophan) attached to a Franz diffusion cell. According to some embodiments, permeation and retention are determined using human cadaver skin attached to a Franz diffusion cell. According to some embodiments, the retained concentration is correlated to the minimum effective concentration.

According to some embodiments, the composition can be applied directly to skin. According to some embodiments, the surface area of the skin ranges from small to large. According to some embodiments, the surface area of the skin ranges from 0.5 cm$^2$ to at least 1000 cm$^2$. According to some embodiments, the surface area is at least 0.5 cm$^2$, at least 1 cm$^2$, at least 10 cm$^2$, at least 20 cm$^2$, at least 30 cm$^2$, at least 40 cm$^2$, at least 50 cm$^2$, at least 60 cm$^2$, at least 70 cm$^2$, at least 80 cm$^2$, at least 90 cm$^2$, at least 100 cm$^2$, at least 200 cm$^2$, at least 300 cm$^2$, at least 400 cm$^2$, at least 500 cm$^2$, at least 600 cm$^2$, at least 700 cm$^2$, at least 800 cm$^2$, at least 900 cm$^2$, or at least 1000 cm$^2$.

Optionally, the film can be applied to a substrate and the substrate containing the film then applied to skin. According to some embodiments, the substrate is a backing layer or backing covered with a release liner for topical application. According to some embodiments, the substrate containing the film can be trimmed to a desired size. According to some embodiments, the substrate may contain therapeutic agents or other components like absorption enhancers/absorbers (which facilitate the absorption through the skin) or occlusive agents (meaning a water-insoluble oily material deposited to hold water in the stratum corneum). Exemplary absorbers include water, laurocapram (Azone), alcohols, fatty alcohols, fatty acids, fatty acid esters, polyols, alkyl methyl sulfoxides, pyrrolidones, anionic surfactants, cationic surfactants, amphoteric surfactants, nonionic surfactants, bile salts, organic acids, and amides. Exemplary occlusive agents include acetylated lanolin alcohol, caprylic/capric triglyceride, cetyl ricinoleate, dimethicone, hydrogenated lanolin, mineral oil, myristol myristate, petrolatum, soybean lipid, and squalene.

According to some embodiments, the backing material or backing is selected so that it is substantially impermeable to the components of the composition. According to some embodiments, the backing and film in combination are biocompatible, non-irritating to the skin, and breathable. According to some embodiments, the backing is made of a sheet or film of a flexible elastomeric material.

For example, backings can be made of a flexible, biocompatible material that imitates the elastic properties of skin and conforms to the skin during movement. According to some embodiments, the backing has a moisture-vapor transmission rate similar to human skin to reduce the risk of an infection.

According to some embodiments, the backing layer is derived from synthetic polymers like polyolefin oils polyester, polyethylene, polyvinylidine chloride, and polyurethane or from natural materials like cotton, wool, etc. Non-occlusive backings allow the area to breathe (i.e., promote water vapor transmission from the skin surface). According to some embodiments, the backing film is an occlusive polyolefin foil (Alevo, Dreieich, Germany). According to some such embodiments, the polyolefin foil is about 0.6 to about 1 mm thick, i.e., at least about 0.6 mm, at least about 0.7 mm, at least about 0.8 mm, at least about 0.9 mm, or about 1 mm thick. According to some such embodiments the backing material may contain an absorbant material separated by a thin poly film. Other exemplary backings are commercially available; for example, suitable backings can be purchased from 3M (St. Paul, Minn.) and Bertek (St. Albans, Vt.).

According to some embodiments, the film remains in place for at least 1 hour, at least 2 hours, at least 3 hours, at least 4 hours, at least 5 hours, at least 6 hours, at least 7 hours, at least 8, at least 9, at least 10, at least 11, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours, at least 24 hours, at least 25 hours, at least 26 hours, at least 27 hours, at least 28 hours, at least 29 hours, at least 30 hours, at least 31 hours, at least 32 hours, at least 33 hours, at least 34 hours, at least 35 hours, at least 36 hours, at least 37 hours, at least 38 hours, at least 39 hours, at least 40 hours, at least 41 hours, at least 42 hours, at least 43 hours, at least 44 hours, at least 45 hours, at least 46 hours, at least 47 hours, at least 48 hours, at least 49 hours, at least 50 hours, at least 51 hours, at least 52 hours, at least 53 hours, at least 54 hours, at least 55 hours, at least 56 hours, at least 57 hours, at least 58 hours, at least 59 hours, at least 60 hours, at least 61 hours, at least 62 hours, at least 63 hours, at least 64 hours, at least 65 hours, at least 66 hours, at least 67 hours, at least 68 hours, at least 69 hours, at least 70 hours, at least 71 hours, at least 72 hours, at least 73 hours, at least 74 hours, at least 75 hours, at least 76 hours, at least 77 hours, at least 78 hours, at least 79 hours, at least 80 hours, at least 81 hours, at least 82 hours, at least 83 hours, at least 84 hours, at least 85 hours, at least 86 hours, at least 87 hours, at least 88 hours, at least 89 hours, at least 90 hours, at least 91 hours, at least 92 hours, at least 93 hours, at least 94 hours, at least 95 hours, at least 96 hours, at least 97 hours, at least 98 hours, at least 99 hours, at least 100 hours, at least 101 hours, at least 102 hours, at least 103 hours, at least 104 hours, at least 105 hours, at least 106 hours, at least 107 hours, at least at least 108 hours, at least 109 hours, at least 110 hours, at least 111 hours, at least 112 hours, at least 113 hours, at least 114 hours, at least 115 hours, at least 116 hours, at least 117 hours, at least 118 hours, at least 119 hours, or at least 120 hours before it is removed. According to some embodiments, the film diminishes loss of moisture from the skin surface. According to some embodiments, the film is removed by peeling.

According to some embodiments, the copolymer is non-cellulosic. According to some embodiments, the copolymer is nonionic. According to some embodiments, the copolymer is both non-cellulosic and nonionic. According to some embodiments the copolymer is comprised of hydrophobic chains and hydrophilic chains. According to some embodiments, the copolymer is a poloxamer. According to some embodiments, the copolymer is an ethoxylated linear alcohol, a fatty acid ester, an amine derivative, and amide derivative, a polyglucoside, a polyalcohol, an ethoxylated polyalcohol, a thiol, or analogs or derivatives thereof.

According to some embodiments, the non-cellulosic, non-ionic copolymer is present in a concentration of from 1% to 30% w/w of the composition, i.e., at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, or at least 30% w/w of the composition.

Exemplary film forming agents include biodegradable polymers, copolymers, block polymers, including, but not limited to, poly(glycolic acid) (PGA), poly(lactic acid) (PLA), polydioxanes, polyoxalates, poly(.alpha.-esters), polyanhydrides, polyacetates, polycaprolactones, poly(orthoesters), polyamino acids, polyaminocarbonates, polyurethanes, polycarbonates, polyamides, poly(alkyl cyanoacrylates), stereopolymers of L- and D-lactic acid, copolymers of bis(p-carboxyphenoxy) propane acid and sebacic acid, sebacic acid copolymers, copolymers of caprolactone, poly (lactic acid)/poly(glycolic acid)/polyethyleneglycol copolymers, copolymers of polyurethane and poly(lactic acid), copolymers of polyurethane and poly(lactic acid), copolymers of .alpha.-amino acids, copolymers of .alpha.-amino acids and caproic acid, copolymers of .alpha.-benzyl glutamate and polyethylene glycol, copolymers of succinate and poly(glycols), polyphosphazene, polyhydroxy-alkanoates, and any combinations thereof.

According to some embodiments, the film forming agent is selected from the group consisting of polyvinyl alcohol, polyvinyl pyrrolidone (copovidone), carrageenan, gelatin, dextrin, polyethylene oxide, guar gum, ghatty gum, xanthan gum, Tragacanth gum, cellulose derivatives, including hydroxyethyl cellulose, ethylcellulose, carboxymethylcellulose, hydroxypropylcellulose, polyvinyl alcohol-polyethylene glycol co-polymers, methacrylic acid-ethyl acrylate copolymers, methacrylic acid and methacrylate based polymers, methylmethacrylate copolymers, and mixtures thereof.

According to some embodiments, the film forming agent is present at a concentration of from 1% to 80% w/w of the composition, i.e., at least 1%, at least 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, at least 50%, at least 55%, at least 60%, at least 65%, at least 70%, at least 75%, or at least 80% w/w of the composition.

Exemplary plasticizers include, without limitation, phthalic anhydride esters, esters of adipic acid, epoxidized esters, trimellitic esters, triacetin, N-methyl-2-pyrrolidone, glycerol formaldehyde, triethyl citrate (TEC), acetyltributylcitrate, ethanol, and polyethylene glycol.

According to some embodiments, the plasticizer is triacetin, triethyl citrate, acetyl triethyl citrate, tributyl citrate, acetyl tributyl citrate, trimethyl citrate, other citrate esters, glycerin, sorbitol, polyalkylene oxides, such as polyethylene glycols, polypropylene glycols, polyethylene-propylene glycols, organic plasticizers with low molecular weights, such as glycerol, glycerol monoacetate, diacetate or polysorbate, cetyl alcohol, or sodium diethylsulfosuccinate.

According to some embodiments, the plasticizer is present at a concentration of from 1% to 20% w/w of the composition, i.e., at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, or at least 20% w/w of the composition.

Non-limiting examples of penetration enhancers include dimethylsulfoxide (DMSO), dimethyl formamide (DMF), allantoin, urazole, N,N-dimethylacetamide (DMA), decylmethylsulfoxide (C10 MSO), polyethylene glycol monolaurate (PEGML), propylene glycol (PG), propylene glycol monolaurate (PGML), glycerol monolaurate (GML), lecithin, the 1-substituted azacycloheptan-2-ones, e.g., 1-n-dodecylcyclazacycloheptan-2-one (available under the trademark Azone® from Whitby Research Incorporated, Richmond, Va.), alcohols, and the like. The penetration enhancer may also be a vegetable oil, for example, safflower oil, cottonseed oil and corn oil. Additional penetration enhancers may generally be found in Remington's Pharmaceutical Sciences, 18th or 19th editions, published by the Mack Publishing Company of Easton, Pa. which is incorporated herein by reference.

According to some embodiments, the permeation enhancer is isopropyl palmitate, isopropyl myristate, isopropyl stearate, propylene glycol, octyl stearate, tridecyl neopentanoate, benzyl alcohol, linoleic acid, alpha-linolenic, oleic acid, cod-liver-oil, methanol, menthol derivatives, squalene, glycerol derivatives, urea, sodium taurocholate, or a combination thereof.

Exemplary anti-oxidants include ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the tradename Trolox®), gallic acid and its alkyl esters, especially propyl gallate, uric acid and its salts and alkyl esters, sorbic acid and its salts, lipoic acid, amines (e.g., N,N-diethylhydroxylamine, aminoguanidine), sulfhydryl compounds (e.g., glutathione), dihydroxy fumaric acid and its salts, glycine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts.

According to some embodiments, the antioxidant is alpha tocopherol (Vitamin-E), ascorbic acid, ascorbic acid esters, glutathione, lipoic acid, uric acid, carotenes, propyl gallate, sodium bisulfite, sodium sulfite, butylated hydroxytoluene (BHT), butylated hydroxyanisole (BHA), or cysteine.

According to some embodiments, the antioxidant is present at a concentration from 0.1% to 10% w/w of the composition, i.e., at least 0.1%, at least 0.2%, at least 0.3%, at least 0.4%, at least 0.5%, at least 0.6%, at least 0.7%, at least 0.8%, at least 0.9%, at least 1%, at least 1.5%, at least 2%, at least 2.5%, at least 3%, at least 3.5%, at least 4%, at least 4.5%, at least 5%, at least 5.5%, at least 6%, at least 6.5%, at least 7%, at least 7.5%, at least 8%, at least 8.5%, at least 9%, at least 9.5%, or at least 10% w/w of the composition.

According to some embodiments, the solvent comprises an organic solvent and water. According to some embodiments, the solvent comprises a non-aqueous hydroalcoholic solvent. Examples of hydroalcoholic solvent include polyhydric alcohol, glycerin, ethylene glycol, dipropylene glycol, hexylene glycol, or a mixture thereof.

According to some embodiments, the solvent is present at a concentration of from 10% to 90% w/w of the composition, i.e., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, or at least 90% w/w of the composition.

The film-forming compositions may be sterilized and if desired, mixed with auxiliary agents, e.g., lubricants, preservatives, stabilizers, wetting agents, emulsifiers, salts for influencing osmotic pressure, buffers, colorants, flavorants and/or fragrances and the like which do not deleteriously react with the active compounds.

Delivery System

According to another aspect, the described invention provides a delivery system which acts as a vehicle for local delivery of therapeutic agents to the skin. According to some embodiments, the delivery system comprises (1) a bioadhesive film-forming pharmaceutical composition for topical delivery comprising: (a) a therapeutic amount of an active agent; and (b) one or more excipients selected from the group consisting of a non-cellulosic polymer or copolymer, a film forming agent, a plasticizer, a permeation enhancer, an antioxidant, an antimicrobial agent, a preservative, a solubilizer, a phase transfer catalyst, a viscosity modifier, a vitamin, a mineral nutrient, a solvent, a colorant and a fragrance; and (2) a means for delivering the composition to a surface of the skin, either directly or indirectly.

A delivery apparatus facilitates targeted delivery of the film-forming pharmaceutical composition. According to some embodiments, the delivery apparatus comprises a first chamber housing a first phase of the composition, and a second chamber housing a second phase of the composition, the first chamber and second chamber being connectively linked; at the appropriate time, the first chamber and second chamber can be connected so that the first phase and the second phase are mixed together to form the composition. According to some embodiments, the delivery apparatus for delivering the film-forming pharmaceutical composition to the skin is an applicator. According to some embodiments, the applicator is a bottle comprising an internal ampule, such that the first phase is separated from the second phase until the internal ampule is broken, releasing the second phase into the first phase, and causing mixing of the phases to form the composition. According to some embodiments, the applicator comprises an applicator tip. Exemplary applicators include, without limitation, atomizers, containers having an apical manual pump, rollette bottles, and tube containers.

Exemplary active agents include, without limitation, analgesic agents, anesthetic agents; anti-acne agents; antibiotic agents; anti-fungal agents; anti-histamines, anti-inflammatory agents (steroidal and non-steroidal); anti-oxidant agents; nicotinic receptor agonists, anti-protozoal agents; anti-pruritic agents; anti-viral agents; chemotherapeutic agents, immunomodulatory agents, keratolytic agents, anti-aging agents, retinoids, and wound healing agents, among others.

According to some embodiments, the active agent can be an analgesic. Exemplary analgesics include non-steroidal anti-inflammatory drugs (NSAIDS), e.g., paracetamol (acetaminophen), ibuprofen, naproxen, and, COX-2 inhibitors, opioids, flupirtine, and specific agents including, but not limited to tricyclic antidepressants, such as amitriptyline, nefopam, and anticonvulsants, including carbamazepine, gabapentin, and pregabalin.

Non-limiting examples of anesthetic agents include lidocaine, bupivacaine, chlorprocaine, dibucaine, etidocaine, mepivacaine, tetracaine, dyclonine, hexylcaine, procaine, cocaine, ketamine, pramoxine and phenol.

Exemplary anti-acne agents include sulfur, glycolic, pyruvic acid, resorcinol, N-acetylcysteine, picolinic acid, picolinic acid derivatives, picolinic acid analogs, benzoyl peroxide, retinoids such as retinoic acid and its derivatives (e.g., cis and trans, esters), and antibiotic agents in the tetracycline-class of antibiotics (e.g., minocycline).

Exemplary classes of antibiotic agents include, without limitation, β-lactams; cephalosporins, fluoroquinolones, aminoglycosides, minobactams, catbapenems, and macrolides. Others include, without limitation, vancomycin, rifampin, doxycycline, linezolid, tetracyclines, trimethoprim/sulfamethoxacole, natural or synthetic ant-infective peptides (see e.g., Kang, H K et al, "Marine peptides and their anti-infective activities," Mar. Drugs 13: 618-54 (2015)) and their glycosylated, phosphorylated, or glycosylated and phosphorylated derivatives (see e.g., Malkoski, M. et al, "Kappacin, a novel antibacterial peptide from bovine milk," Antimicrob. Agents & Chemother. 45(8): 2309-15 (2001), Strub, M et al., "Antibacterial activity of glycosylated and phosphorylated chromogranin A-derived peptide 173-194 from bovine adrenal medullary chromaffin granules," J. Biol. Chem. 271(45): 28533-40 (1996)) and anti-infective monoclonal antibody cocktails (see e.g., Saylor, C. et al., "Monoclonal antibody-based therapies for microbial diseases," Vaccine 27 (Suppl. 6): G38-G46 (2009)).

Exemplary beta-lactam antibiotic agents include penicillin g, penicillin-vk, methicillin, nafcillin, oxacillin, cloxacillin; dicloxacillin, amoxicillin; ticarcillin; carbenicillin; mezlocillin; azlocillin; and piperacillin. exemplary cephalosporins include cephalothin, cefazolin, cephaprin, cephalexin, cefaclor, cefotetan, ceftriaxone, cefpirome, cefepime, cefoxitin; cefuroxime; cefonicid, cefmetazole; cefotetan; cefprozil; cefetamet; cefoperazone; cefotaxime; ceftizoxime; ceftriaxone; ceftazidime; cefixime; cefpodoxime; and cefsulodin. Exemplary fluoroquinolones include nalidixic acid, ciprofloxacin, levofloxacin, moxifloxacin, ofloxacin; enoxacin; lomefloxacin; cinoxacin and norfloxacin. Exemplary aminoglycosides include amikacin, gentamicin, kanamycin, neomycin, and tobramycin. Exemplary monobactams include aztreonam, tigemonam, nocardicin a, and tabtoxin. Exemplary carbapenams include aztreonam, ertapenem, imipenem, and meropenem. Exemplary macrolides include azithromycin, clarithromycin, dirithromycin, erythromycin, erythromycin estolate; erythromycin ethyl succinate; erythromycin glucoheptonate; erythromycin lactobionate; erythromycin stearate and clindamycin. Exemplary tetracyclines include tetracycline, chloretracycline, oxyetracycline, demeclocycline, lymecycline, meclocycline, methacycline, minocycline, and rolitetracycline.

Exemplary anti-fungal agents include amphotericin b, candicidin, dermostatin, filipin, fungichromin, hachimycin, hamycin, lucensomycin, mepartricin, natamycin, nystatin, pecilocin, perimycin, azaserine, griseofulvin, oligomycins, neomycin, pyrrolnitrin, siccanin, tubercidin, viridin, butenafine, naftifine, terbinafine, bifonazole, butoconazole, chlordantoin, chlormidazole, cloconazole, clotrimazole, econazole, enilconazole, fenticonazole, flutrimazole, isoconazole, ketoconazole, lanoconazole, miconazole, omoconazole, oxiconazole, sertaconazole, sulconazole, tioconazole, tolciclate, tolindate, tolnaftate, fluconazole, itraconazole, saperconazole, terconazole, acrisorcin, amorolfine, biphenamine, bromosalicylchloranilide, buclosamide, calcium propionate, chlorphenesin, ciclopirox, cloxyquin, coparaffinate, diamthazole, exalamide, flucytosine, halethazole, hexetidine, loflucarban, nifuratel, potassium iodide, propionic acid, pyrithione, salicylanilide, sodium propionate, sulbentine, tenonitrozole, triacetin, ujothion, undecylenic acid, and zinc propionate.

An exemplary nicotinic receptor agonist is nicotine. According to some embodiments, the nicotine is in a base form. According to some embodiments, the nicotine is in a salt form.

Exemplary anti-protozoal agents include pyrimethamine (Daraprim®) sulfadiazine, and leucovorin.

Exemplary antipruritic agents include hydroxyzine, methdilazine, and trimeprazine.

Exemplary anti-viral agents include acyclovir, cidofovir, cytarabine, dideoxyadenosine, didanosine, edoxudine, famciclovir, floxuridine, ganciclovir, idoxuridine, inosine pranobex, lamivudine, madu, penciclovir, sorivudine, stavudine, trifluridine, valacyclovir, vidarabine, zaicitabine, acemannan, acetylleucine, amantadine, amidinomycin, delavirdine, foscamet, indinavir, interferons (e.g., ifn-alpha), kethoxal, lysozyme, methisazone, moroxydine, nevirapine, podophyllotoxin, ribavirin, rimantadine, ritonavir2, saquinavir, stailimycin, statolon, tromantadine, zidovudine (azt) and xenazoic acid.

According to some embodiments, an immunomodulatory agent is an immunosuppressant. Exemplary immunosuppressants include glucocorticoids, calcineurin inhibitors, and antiproliferative/antimetabolic agents. Non-limiting examples of glucocorticoids include prednisone, prednisolone, methylprednisilone, dexamethasone, and hydrocortisone. Non-limiting examples of calcineurin inhibitors include cyclosporine and tacrolimus. Non-limiting examples of antiproliferative/antimetabolic agents include rapamycin, azathioprine, and mycophenolate mofetil.

Exemplary local anesthetics include, ambucaine, amolanone, amylcaine, benoxinate, benzocaine, betoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethisoquin, dimethocaine, diperodon, dyclonine, ecogonidine, ecogonine, euprocin, fenalcomine, formocaine, hexylcaine, hydroxyteteracaine, isobutyl p-aminobenzoate, leucinocaine, levoxadrol, lidocaine, mepivacaine, meprylcaine, metabutoxycaine, methyl chloride, myrtecaine, naepaine, octacaine, orthocaine, oxethazaine, parenthoxycaine, phenacaine, phenol, piperocaine, piridocaine, polidocanol, pramoxine, prilocaine, procaine, propanocaine, paracaine, propipocaine, propoxycaine, pseudococaine, pyrrocaine, ropivacaine, salicyl alcohol, tetracaine, tolycaine, trimecaine, zolamine, or a pharmaceutically acceptable salt thereof, or a mixture thereof. Amide type local anesthetics are characterized by an amide functionality, while ester type local anesthetics contain an ester functionality. Exemplary amide type local anesthetics include lidocaine, bupivacaine, prilocaine, mepivacaine, etidocaine, ropivacaine, dibucaine, and mixtures thereof. Exemplary ester type local anesthetics include tetracaine, procaine, benzocaine, chloroprocaine, their pharmaceutically acceptable salt, or a mixture thereof.

Exemplary chemotherapeutic agents include, without limitation, temozolomide, busulfan, ifosamide, melphalan, carmustine, lomustine, mesna, 5-fluorouracil, capecitabine, gemcitabine, floxuridine, decitabine, mercaptopurine, pemetrexed disodium, methotrexate, vincristine, vinblastine, vinorelbine tartrate, paclitaxel, docetaxel, ixabepilone, daunorubicin, epirubicin, doxorubicin, idarubicin, amrubicin, pirarubicin, mitoxantrone, etoposide, etoposide phosphate, teniposide, mitomycin C, actinomycin D, colchicine, topotecan, irinotecan, gemcitabine cyclosporin, verapamil, valspodor, probenecid, biricodar, terfenadine, quinidine, and pervilleine A.

Non-limiting examples of non-steroidal anti-inflammatory include, ibuprofen (Advil®), naproxen sodium (Aleve®), and acetaminophen (Tylenol®), oxicams, such as piroxicam, isoxicam, tenoxicam, sudoxicam, and CP-14, 304; disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents also may be employed, as well as the dermatologically acceptable salts and esters of these agents. For example, etofenamate, a flufenamic acid derivative, can be used for topical application.

Non-limiting examples of steroidal anti-inflammatory agents include corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflucortolone valerate, fluadrenolone, fluclorolone acetonide, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflorosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

Non-limiting examples of vitamins and nutrients usable in context of the present invention include vitamin A and its analogs and derivatives: retinol, retinal, retinyl palmitate, retinoic acid, tretinoin, iso-tretinoin (known collectively as retinoids), vitamin E (tocopherol and its derivatives), vitamin C (L-ascorbic acid and its esters and other derivatives), vitamin B3 (niacinamide and its derivatives), alpha hydroxy acids (such as glycolic acid, lactic acid, tartaric acid, malic acid, citric acid, etc.) and beta hydroxy acids (such as salicylic acid and the like).

Non-limiting examples of minerals and salts include, for example, sodium, potassium, calcium, magnesium, copper, manganese, molybdenum, selenium, silicon, iron, zinc, vanadium, boron, cobalt, iodine, chromium and tin. Minerals or salts can be provided as organic (organic acids) or inorganic salts (e.g., chlorides, sulfates, phosphates or nitrates). In a non-limiting example, a selenium salt is sodium selenite. Amounts or concentrations of minerals or salts will depend upon the particular mineral or salt.

Nonlimiting examples of retinoids include retinol, retinal, tretinoin, isotretinoin, alitretinoin, etretinate, acitretin, tazarotene, bexarotene, and adapalene.

According to some embodiments, the composition is an aseptic composition. According to some embodiments, the composition is a wound healing composition.

According to some embodiments, film formation occurs at room temperature. According to some embodiments, because the film is pliant, it adheres and conforms to surfaces of the skin. According to some embodiments, the film resists breaking under tension, i.e., has tensile strength. According to some embodiments, the film may be of any order release kinetics, including zero order release, first order release, second order release, delayed release, sustained release, immediate release, etc., and any combination thereof. The film-forming composition may further include any of those materials routinely used in the art of pharmacy and medicine, including, but not limited to, erodible, non-erodible, biodegradable, or nonbiodegradable material or combinations thereof. According to some embodiments, the film may be of virtually any shape. According to some embodiments, the film, once formed is removable without leaving a substantial residue.

According to some embodiments, the film comprises a matrix. According to some embodiments, the active agent releases from the film by diffusion according to Ficke's law. Accordingly, thickness of the film is not a consideration. According to some embodiments, the release is a controlled release. According to some embodiments, the release is a delayed release. According to some embodiments, the release is a sustained release.

According to some embodiments, the composition is characterized by controlled release of locally sustained levels of a minimum effective concentration (MEC) of the active agent. According to some embodiments the MEC remains in the tissue between applications. According to some embodiments, the composition is pliant (meaning having a quality or tendency to bend that does not require force or pressure from the outside.

The intensity of effect of a drug (y-axis) can be plotted as a function of the dose of drug administered (X-axis). Goodman & Gilman's The Pharmacological Basis of Therapeutics, Ed. Joel G. Hardman, Lee E. Limbird, Eds., 10th Ed., McGraw Hill, New York (2001), p. 25, 50). These plots are referred to as dose-effect curves. Such a curve can be resolved into simpler curves for each of its components. These concentration-effect relationships can be viewed as having four characteristic variables: potency, slope, maximal efficacy, and individual variation.

The location of the dose-effect curve along the concentration axis is an expression of the potency of a drug. Id. If the drug is to be administered by transdermal absorption, a highly potent drug is required, since the capacity of the skin to absorb drugs is limited.

According to some embodiments, potency of the active agent in the claimed composition is maintained within a range of from 90% to 250%, at least: 90%, 91%, 92%, 93%, 94%, 95%, 96%, 97%, 98%, 99%, 100%, 110%, 120%, 130%, 140%, 150%, 160%, 170%, 180%, 190%, 200%, 210%, 220%, 230%, 240%, or 250%.

The slope of the dose-effect curve reflects the mechanism of action of a drug. The steepness of the curve dictates the range of doses useful for achieving a clinical effect.

Maximal or clinical efficacy refers to the maximal effect that can be produced by a drug. Maximal efficacy is determined principally by the properties of the drug and its receptor-effector system and is reflected in the plateau of the curve. In clinical use, a drug's dosage may be limited by undesired effects.

Biological variability. An effect of varying intensity may occur in different individuals at a specified concentration or a drug. It follows that a range of concentrations may be required to produce an effect of specified intensity in all subjects.

Lastly, different individuals may vary in the magnitude of their response to the same concentration of a drug when the appropriate correction has been made for differences in potency, maximal efficacy and slope.

The duration of a drug's action is determined by the time period over which concentrations exceed the MEC. Following administration of a dose of drug, its effects usually show a characteristic temporal pattern. A plot of drug effect vs. time illustrates the temporal characteristics of drug effect and its relationship to the therapeutic window. A lag period is present before the drug concentration exceeds the minimum effective concentration (MEC) for the desired effect. Following onset of the response, the intensity of the effect increases as the drug continues to be absorbed and distributed. This reaches a peak, after which drug elimination results in a decline in the effect's intensity that disappears when the drug concentration falls back below the MEC. The therapeutic window reflects a concentration range that provides efficacy without unacceptable toxicity. Accordingly another dose of drug should be given to maintain concentrations within the therapeutic window.

According to some embodiments, the concentration of the active agent is at least 1% w/w of the composition, at least 2% w/w of the composition, at least 3% w/w of the composition, at least 4% w/w of the composition, at least 5% w/w of the composition, at least 6% w/w of the composition, at least 7% w/w of the composition, at least 8% w/w of the composition, at least 9% w/w of the composition, at least 10% w/w of the composition; at least 11% w/w of the composition; at least 12% w/w of the composition; at least 13% w/w of the composition; at least 14% w/w of the composition; at least 15% w/w of the composition; at least 16% w/w of the composition; at least 17% w/w of the composition; at least 18% w/w of the composition; at least 19% w/w of the composition; at least 20% w/w of the composition; at least 30% w/w of the composition, at least 40% w/w of the composition, at least 50% w/w of the composition, or at least 60% w/w of the composition. According to some embodiments, the concentration of the active agent is from about 1% to about 10% w/w of the composition, i.e., at least 1%, at least 2%, at least 3%, at least 4%, at least 5%, at least 6%, at least 7%, at least 8%, at least 9%, or at least 10% w/w of the composition.

According to some embodiments, the content of the active agent retained on skin and its permeation/flux into the skin can be measured as a function of time. According to some embodiments, flux is determined using one of many available artificial membranes (e.g., Cuprophan) attached to a Franz diffusion cell. According to some embodiments, permeation and retention are determined using human cadaver skin attached to a Franz diffusion cell. According to some embodiments, the retained concentration is correlated to the minimum effective concentration.

According to some embodiments, the composition can be applied directly to skin. According to some embodiments, the surface area of the skin ranges from small to large According to some embodiments the surface area ranges from 0.5 cm$^2$ to at least 1000 cm$^2$. According to some embodiments, the surface area is at least 0.5 cm$^2$, at least 1 cm$^2$, at least 10 cm$^2$, at least 20 cm$^2$, at least 30 cm$^2$, at least 40 cm$^2$, at least 50 cm$^2$, at least 60 cm$^2$, at least 70 cm$^2$, at least 80 cm$^2$, at least 90 cm$^2$, at least 100 cm$^2$, at least 200 cm$^2$, at least 300 cm$^2$, at least 400 cm$^2$, at least 500 cm$^2$, at least 600 cm$^2$, at least 700 cm$^2$, at least 800 cm$^2$, at least 900 cm$^2$, or 1000 cm$^2$.

Optionally, the delivery system can comprise a substrate to which the film-forming pharmaceutical composition is applied; once the film forms, the substrate containing the film is then applied to skin. According to some embodiments, the substrate is a backing layer or backing covered with a release liner for topical application. According to some embodiments, the substrate containing the film can be trimmed to a desired size. According to some embodiments, the substrate may contain one or more therapeutic agents. According to some embodiments, the substrate may contain one or more other components such as an absorber or an occlusive agent. Exemplary absorbers include water, laurocapram (Azone), alcohols, fatty alcohols, fatty acids, fatty acid esters, polyols, alkyl methyl sulfoxides, pyrrolidones, anionic surfactants, cationic surfactants, amphoteric surfactants, nonionic surfactants, bile salts, organic acids, and amides. Exemplary occlusive agents include acetylated lanolin alcohol, caprylic/capric triglyceride, cetyl ricinoleate, dimethicone, hydrogenated lanolin, mineral oil, myristol myristate, petrolatum, soybean lipid, and squalene.

According to some embodiments, the backing material or backing is selected so that it is substantially impermeable to the components of the composition. According to some embodiments, the backing and film in combination are biocompatible, non-irritating to the skin, and breathable. According to some embodiments, the backing is made of a sheet or film of a flexible elastomeric material.

For example, backings can be made of a flexible, biocompatible material that imitates the elastic properties of skin and conforms to the skin during movement. According to some embodiments, the backing has a moisture-vapor transmission rate similar to human skin to reduce the risk of an infection.

According to some embodiments, the backing layer is derived from synthetic polymers like polyolefin oils polyester, polyethylene, polyvinylidine chloride, and polyurethane or from natural materials like cotton, wool, etc. Non-occlusive backings allow the area to breathe (i.e., promote water vapor transmission from the skin surface). According to some embodiments, the backing film is an occlusive polyolefin foil (Alevo, Dreieich, Germany). According to some such embodiments, the polyolefin foil is about 0.6 to about 1 mm thick. According to some such embodiments the backing material comprises an absorbant material separated by a thin poly film. Other exemplary backings are commercially available; for example, suitable backings can be purchased from 3M (St. Paul, Minn.) and Bertek (St. Albans, Vt.).

According to some embodiments, the film remains in place for at least 1 hour, at least 2 hours, at least 3 hours, at least 4 hours, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours, at least 24 hours, at least 25 hours, at least 26 hours, at least 27 hours, at least 28 hours, at least 29 hours, at least 30 hours, at least 31 hours, at least 32 hours, at least 33 hours, at least 34 hours, at least 35 hours, at least 36 hours, at least 37 hours, at least 38 hours, at least 39 hours, at least 40 hours, at least 41 hours, at least 42 hours, at least 43 hours, at least 44 hours, at least 45 hours, at least 46 hours, at least 47 hours, at least 48 hours, at least 49 hours, at least 50 hours, at least 51 hours, at least 52 hours, at least 53 hours, at least 54 hours, at least 55 hours, at least 56 hours, at least 57 hours, at least 58 hours, at least 59 hours, at least 60 hours, at least 61 hours, at least 62 hours, at least 63 hours, at least 64 hours, at least 65 hours, at least 66 hours, at least 67 hours, at least 68 hours, at least 69 hours, at least 70 hours, at least 71 hours, at least 72 hours, at least 73 hours, at least 74 hours, at least 75 hours, at least 76 hours, at least 77 hours, at least 78 hours, at least 79 hours, at least 80 hours, at least 81 hours, at least 82 hours, at least 83 hours, at least 84 hours, at least 85 hours, at least 86 hours, at least 87 hours, at least 88 hours, at least 89 hours, at least 90 hours, at least 91 hours, at least 92 hours, at least 93 hours, at least 94 hours, at least 95 hours, at least 96 hours, at least 97 hours, at least 98 hours, at least 99 hours, at least 100 hours, at least 101 hours, at least 102 hours, at least 103 hours, at least 104 hours, at least 105 hours, at least 106 hours, at least 107 hours, at least at least 108 hours, at least 109 hours, at least 110 hours, at least 111 hours, at least 112 hours, at least 113 hours, at least 114 hours, at least 115 hours, at least 116 hours, at least 117 hours, at least 118 hours, at least 119 hours, or at least 120 hours before it is removed. According to some embodiments, the film diminishes loss of moisture from the skin surface. According to some embodiments, the film is removed by peeling.

According to some embodiments, the copolymer is non-cellulosic. According to some embodiments, the copolymer is nonionic. According to some embodiments, the copolymer is both non-cellulosic and nonionic. According to some embodiments the copolymer is comprised of hydrophobic chains and hydrophilic chains. According to some embodiments, the copolymer is a poloxamer. According to some embodiments, the copolymer is an ethoxylated linear alcohol, a fatty acid ester, an amine derivative, and amide derivative, a polyglucoside, a polyalcohol, an ethoxylated polyalcohol, a thiol, or analogs or derivatives thereof.

According to some embodiments, the non-cellulosic, non-ionic copolymer is present in a concentration of from 1% to 30% w/w of the composition, i.e., at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, or at least 30% w/w of the composition.

Exemplary film forming agents include biodegradable polymers, copolymers, block polymers, including, but not limited to, poly(glycolic acid) (PGA), poly(lactic acid) (PLA), polydioxanes, polyoxalates, poly(.alpha.-esters), polyanhydrides, polyacetates, polycaprolactones, poly(orthoesters), polyamino acids, polyaminocarbonates, polyurethanes, polycarbonates, polyamides, poly(alkyl cyanoacrylates), stereopolymers of L- and D-lactic acid, copolymers of bis(p-carboxyphenoxy) propane acid and sebacic acid, sebacic acid copolymers, copolymers of caprolactone, poly(lactic acid)/poly(glycolic acid)/polyethyleneglycol copolymers, copolymers of polyurethane and poly(lactic acid), copolymers of polyurethane and poly(lactic acid), copolymers of .alpha.-amino acids, copolymers of .alpha.-amino acids and caproic acid, copolymers of .alpha.-benzyl glutamate and polyethylene glycol, copolymers of succinate and poly(glycols), polyphosphazene, polyhydroxy-alkanoates, and any combinations thereof.

According to some embodiments, the film forming agent is selected from the group consisting of polyvinyl alcohol, polyvinyl pyrrolidone (copovidone), carrageenan, gelatin, dextrin, polyethylene oxide, guar gum, xanthan gum, Tragacanth gum, cellulose derivatives, including hydroxyethyl cellulose, ethylcellulose, carboxymethylcellulose, hydroxypropylcellulose, polyvinyl alcohol-polyethylene glycol co-polymers, methacrylic acid-ethyl acrylate copolymers, methacrylic acid and methacrylate based polymers, methylmethacrylate copolymers, and mixtures thereof.

According to some embodiments, the film forming agent is present at a concentration of from 1% to 80% w/w of the composition, i.e., at least 1%, at least 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, at least 50%, at least 55%, at least 60%, at least 65%, at least 70%, at least 75%, or at least 80% w/w of the composition.

Exemplary plasticizers include, without limitation, phthalic anhydride esters, esters of adipic acid, epoxidized esters, trimellitic esters, triacetin, N-methyl-2-pyrrolidone, glycerol formaldehyde, triethyl citrate (TEC), acetyltributylcitrate, ethanol, and polyethylene glycol.

According to some embodiments, the plasticizer is triacetine, triethyl citrate, acetyl triethyl citrate, tributyl citrate, acetyl tributyl citrate, trimethyl citrate, other citrate esters, glycerin, sorbitol, polyalkylene oxides, such as polyethylene glycols, polypropylene glycols, polyethylene-propylene glycols, organic plasticizers with low molecular weights, such as glycerol, glycerol monoacetate, diacetate or polysorbate, cetyl alcohol, or sodium diethylsulfosuccinate.

According to some embodiments, the plasticizer is present at a concentration of from 1% to 20% w/w of the composition, i.e., at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, or at least 20% w/w of the composition.

Non-limiting examples of penetration enhancers include dimethylsulfoxide (DMSO), dimethyl formamide (DMF), allantoin, urazole, N,N-dimethylacetamide (DMA), decylmethylsulfoxide (C10 MSO), polyethylene glycol monolaurate (PEGML), propylene glycol (PG), propylene glycol monolaurate (PGML), glycerol monolaurate (GML), lecithin, the 1-substituted azacycloheptan-2-ones, e.g., 1-n-dodecylcyclazacycloheptan-2-one (available under the trademark Azone® from Whitby Research Incorporated, Richmond, Va.), alcohols, and the like. The penetration enhancer may also be a vegetable oil, for example, safflower oil, cottonseed oil and corn oil. Additional penetration enhancers may generally be found in Remington's Pharmaceutical Sciences, 18th or 19th editions, published by the Mack Publishing Company of Easton, Pa. which is incorporated herein by reference.

According to some embodiments, the permeation enhancer is isopropyl palmitate, isopropyl myristate, isopropyl stearate, propylene glycol, octyl stearate, tridecyl neopentanoate, benzyl alcohol, linoleic acid, alpha-linolenic, oleic acid, cod-liver-oil, methanol, menthol derivatives, squalene, glycerol derivatives, urea, sodium taurocholate, or a combination thereof.

Exemplary anti-oxidants include ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5,7,8-tetramethylchroman-2-carboxylic acid (commercially available under the tradename Trolox®), gallic acid and its alkyl esters, especially propyl gallate, uric acid and its salts and alkyl esters, sorbic acid and its salts, lipoic acid, amines (e.g., N,N-diethylhydroxylamine, aminoguanidine), sulfhydryl compounds (e.g., glutathione), dihydroxy fumaric acid and its salts, glycine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts.

According to some embodiments, the antioxidant is alpha tocopherol (Vitamin-E), ascorbic acid, ascorbic acid esters, glutathione, lipoic acid, uric acid, carotenes, propyl gallate, sodium bisulfite, sodium sulfite, butylated hydroxytoluene (BHT), butylated hydroxyanisole (BHA), or cysteine.

According to some embodiments, the antioxidant is present at a concentration from 0.1% to 10% w/w of the composition, i.e., at least 0.1%, at least 0.2%, at least 0.3%, at least 0.4%, at least 0.5%, at least 0.6%, at least 0.7%, at least 0.8%, at least 0.9%, at least 1%, at least 1.5%, at least 2%, at least 2.5%, at least 3%, at least 3.5%, at least 4%, at least 4.5%, at least 5%, at least 5.5%, at least 6%, at least 6.5%, at least 7%, at least 7.5%, at least 8%, at least 8.5%, at least 9%, at least 9.5%, or at least 10% w/w of the composition.

According to some embodiments, the solvent comprises an organic solvent and water. According to some embodiments, the solvent comprises a non-aqueous hydroalcoholic solvent. According to some embodiments, the hydroalcoholic solvent is polyhydric alcohol, glycerin, ethylene glycol, dipropylene glycol, hexylene glycol, or mixtures thereof.

According to some embodiments, the solvent is present at a concentration of from 10% to 90% w/w of the composition, i.e., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, or at least 90% w/w of the composition.

The film-forming compositions may be sterilized and if desired, mixed with auxiliary agents, e.g., lubricants, preservatives, stabilizers, wetting agents, emulsifiers, salts for influencing osmotic pressure, buffers, colorants, flavorants and/or fragrances and the like which do not deleteriously react with the active compounds.

Uses of the Delivery System

According to another aspect, the delivery system can be used in the manufacture of a medicament for treating a skin condition, disease or disorder. A therapeutic amount of the pharmaceutical composition can be effective to treat such skin disorders as pruritus, atopic dermatitis, psoriasis, acne, skin infections, skin infestations, skin neoplasms; wounds to the skin, and skin manifestations of autoimmune disorders.

According to some embodiments, the applying of the bioadhesive film-forming composition can be directly to skin. According to some embodiments, the surface area of the skin ranges from small to large. According to some embodiments the surface area ranges from 0.5 cm² to at least 1000 cm². According to some embodiments, the surface area is at least 0.5 cm², at least 1 cm², at least 10 cm², at least 20 cm², at least 30 cm², at least 40 cm², at least 50 cm², at least 60 cm², at least 70 cm², at least 80 cm², at least 90 cm², at least 100 cm², at least 200 cm², at least 300 cm², at least 400 cm², at least 500 cm², at least 600 cm², at least 700 cm², at least 800 cm², at least 900 cm², or at least 1000 cm².

Optionally, the applying of the film-forming composition can be to a substrate; once the film forms, the substrate containing the film is then applied to skin. According to some embodiments, the substrate is a backing layer or backing covered with a release liner for topical application. According to some embodiments, the substrate containing the film can be trimmed to a desired size and the substrate may contain therapeutic agents or other components like absorbers or occlusive agents.

According to some embodiments, the backing material or backing is selected so that it is substantially impermeable to the components of the composition. According to some embodiments, the backing and film in combination are biocompatible, non-irritating to the skin, and breathable. According to some embodiments, the backing is made of a sheet or film of a flexible elastomeric material.

For example, backings can be made of a flexible, biocompatible material that imitates the elastic properties of skin and conforms to the skin during movement. According to some embodiments, the backing has a moisture-vapor transmission rate similar to human skin to reduce the risk of an infection.

According to some embodiments, the backing layer is derived from synthetic polymers like polyolefin oils polyester, polyethylene, polyvinylidine chloride, and polyurethane or from natural materials like cotton, wool, etc. Non-occlusive backings allow the area to breathe (i.e., promote water vapor transmission from the skin surface). According to some embodiments, the backing film is an occlusive polyolefin foil (Alevo, Dreieich, Germany). According to some such embodiments, the polyolefin foil is about 0.6 to about 1 mm thick. According to some such embodiments the backing material may have absorbant material separated by a thin poly film. Other exemplary backings are commercially available; for example, suitable backings can be purchased from 3M (St. Paul, Minn.) and Bertek (St. Albans, Vt.).

According to some embodiments, the film remains in place for at least 1 hour, at least 2 hours, at least 3 hours, at least 4 hours, at least 5 hours, at least 6 hours, at least 7 hours, at least 8 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours, at least 24 hours, at least 25 hours, at least 26 hours, at least 27 hours, at least 28 hours, at least 29 hours, at least 30 hours, at least 31 hours, at least 32 hours, at least 33 hours, at least 34 hours, at least 35 hours, at least 36 hours, at least 37 hours, at least 38 hours, at least 39 hours, at least 40 hours, at least 41 hours, at least 42 hours, at least 43 hours, at least 44 hours, at least 45 hours, at least 46 hours, at least 47 hours, at least 48 hours, at least 49 hours, at least 50 hours, at least 51 hours, at least 52 hours, at least 53 hours, at least 54 hours, at least 55 hours, at least 56 hours, at least 57 hours, at least 58 hours, at least 59 hours, at least 60 hours, at least 61 hours, at least 62 hours, at least 63 hours, at least 64 hours, at least 65 hours, at least 66 hours, at least 67 hours, at least 68 hours, at least 69 hours, at least 70 hours, at least 71 hours, at least 72 hours, at least 73 hours, at least 74 hours, at least 75 hours, at least 76 hours, at least 77 hours, at least 78 hours, at least 79 hours, at least 80 hours, at least 81 hours, at least 82 hours, at least 83 hours, at least 84 hours, at least 85 hours, at least 86 hours, at least 87 hours, at least 88 hours, at least 89 hours, at least 90 hours, at least 91 hours, at least 92 hours, at least 93 hours, at least 94 hours, at least 95 hours, at least 96 hours, at least 97 hours, at least 98 hours, at least 99 hours, at least 100 hours, at least 101 hours, at least 102 hours, at least 103 hours, at least 104 hours, at least 105 hours, at least 106 hours, at least 107 hours, at least at least 108 hours, at least 109 hours, at least 110 hours, at least 111 hours, at least 112 hours, at least 113 hours, at least 114 hours, at least 115 hours, at least 116 hours, at least 117 hours, at least 118 hours, at least 119 hours, or at least 120 hours before it is removed. According to some embodiments, the film diminishes loss of moisture from the skin surface. According to some embodiments, the film is removed by peeling.

According to some embodiments, film formation occurs at room temperature. According to some embodiments, because the film is pliant, it adheres and conforms to surfaces of the skin. According to some embodiments, the film resists breaking under tension, i.e., has tensile strength. According to some embodiments, the film may be of any order release kinetics, including zero order release, first order release, second order release, delayed release, sustained release, immediate release, etc., and any combination thereof. The film-forming composition may further include any of those materials routinely used in the art of pharmacy and medicine, including, but not limited to, erodible, non-erodible, biodegradable, or nonbiodegradable material or combinations thereof. According to some embodiments, the film may be of virtually any shape. According to some embodiments, the film, once formed is removable without leaving a substantial residue.

According to some embodiments, the film comprises a matrix. According to some embodiments, the active agent releases from the film by diffusion according to Ficke's law. Accordingly, thickness of the film is not a consideration. According to some embodiments, the release is a controlled release. According to some embodiments, the release is a delayed release. According to some embodiments, the release is a sustained release.

According to some embodiments, the composition is characterized by controlled release of locally sustained levels of a minimum effective concentration (MEC) of the active agent. According to some embodiments the MEC remains in the tissue between applications. According to some embodiments, the composition is pliant (meaning having a quality or tendency to bend that does not require force or pressure from the outside.

According to some embodiments, potency of the active agent in the claimed composition is maintained within a range of from 90% to 250%, at least: 90%, 91%, 92%, 93%, 94%, 95%, 96%, 97%, 98%, 99%, 100%, 110%, 120%, 130%, 140%, 150%, 160%, 170%, 180%, 190%, 200%, 210%, 220%, 230%, 240%, or 250%.

According to some embodiments, the concentration of the active agent is at least 1% w/w of the composition, at least 2% w/w of the composition, at least 3% w/w of the composition, at least 4% w/w of the composition, at least 5% w/w of the composition, at least 6% w/w of the composition, at least 7% w/w of the composition, at least 8% w/w of the composition, at least 9% w/w of the composition, at least 10% w/w of the composition; at least 11% w/w of the composition; at least 12% w/w of the composition; at least 13% w/w of the composition; at least 14% w/w of the composition; at least 15% w/w of the composition; at least 16% w/w of the composition; at least 17% w/w of the composition; at least 18% w/w of the composition; at least 19% w/w of the composition; at least 20% w/w of the composition; at least 30% w/w of the composition; at least 40% w/w of the composition, at least 50% w/w of the composition, or at least 60% w/w of the composition. According to some embodiments, the concentration of the active agent is from about 1% to about 10% w/w of the composition, i.e., at least 1%, at least 2%, at least 3%, at least 4%, at least 5%, at least 6%, at least 7%, at least 8%, at least 9%, or at least 10% w/w of the composition.

According to some embodiments, the content of the active agent retained on skin and its permeation/flux into the skin can be measured as a function of time. According to some embodiments, flux is determined using one of many commercially available artificial membranes (e.g., Cuprophan) attached to a Franz diffusion cell. According to some embodiments, permeation and retention are determined using human cadaver skin attached to a Franz diffusion cell. According to some embodiments, the retained concentration is correlated to the minimum effective concentration.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which can independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the described invention, the preferred methods and materials are now described. All publications mentioned herein are incorporated herein by reference to disclose and described the methods and/or materials in connection with which the publications are cited.

It must be noted that as used herein and in the appended claims, the singular forms "a", "and", and "the" include plural references unless the context clearly dictates otherwise. All technical and scientific terms used herein have the same meaning.

The publications discussed herein are provided solely for their disclosure prior to the filing date of the present application. Nothing herein is to be construed as an admission that the described invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the described invention, and are not intended to limit the scope of what the inventors regard as their invention nor are they intended to represent that the experiments below are all or the only experiments performed. Efforts have been made to ensure accuracy with respect to numbers used (e.g., amounts, temperatures, etc.) but some experimental errors and deviations should be accounted for. Unless indicated otherwise, parts are by weight, molecular weight is weight average molecular weight, temperature is in degrees Centigrade, and pressure is at or near atmospheric.

Exemplary Formulations

Exemplary formulations are prepared according to the following general steps:

Step 1: The active agent and the nonionic copolymer are mixed using heat to get a uniform mix. The mixture of active agent and nonionic copolymer is then added to a portion of solvent to form dispersion.

Step 2: In the second part of the process the film forming agent is dissolved in a portion of solvent.

Step 3: The dispersion of active agent and nonionic copolymer from step 1 is mixed with solution of film forming agent from step 2 under stirring to form a homogenous dispersion.

Step 4: The antioxidant, plasticizer and permeation enhancer is then added to the dispersion of step 3 to form a homogenous film forming formulation.

Test Procedures for Film Attributes:

Weight:

The gel is coated on a silicon coated polyethylene terephthalate (PET) liner using a 10 mil stainless steel ("SS") knife, and allowed to dry in air for 30 minutes at 25° C./60% RH. A film of size 10 cm$^2$ is die cut and weighed on an analytical balance. The weight for 10 samples is recorded and the average value reported.

Thickness:

The gel is coated on a silicon coated PET liner using a 10 mil SS knife, and allowed to dry in air for 30 minutes at 25° C./60% RH. A film of size 10 cm2 is die cut and the thickness measured. The thickness is recorded accordingly for 10 samples and the average value reported.

Folding Endurance:

The gel is coated on a silicon coated PET liner using a 10 mil SS knife, and allowed to dry in air for 30 minutes at 25° C./60% RH. A film of size 10 cm$^2$ is die cut. The film should not break under 150 fold and unfold steps at the same position.

Tensile Break:

The gel is coated on a silicon coated PET liner using a 10 mil SS knife, and allowed to dry in air for 30 minutes at 25° C./60% RH. The tensile break test is performed using a strip measuring 25 mm/100 m using universal testing machine (UTM) manufactured by Hemtech, Vadodara INDIA or equivalent.

Example 1

Table 1 shows a formulation for a film-forming minocycline gel expressed as percent weight/weight (% w/w) of the composition.

TABLE 1

| Ingredients | % w/w |
| --- | --- |
| Minocycline HCL | 4.0 |
| Poloxamer 188 | 8.0 |
| Absolute alcohol | 16.5 |
| Polyvinyl alcohol | 15.0 |
| Sodium sulfite | 4.0 |
| Propyl gallate | 0.1 |
| Tri ethyl citrate | 3.0 |
| Butylated hydroxyl toluene (BHT) | 0.4 |
| Isoproyl myristate | 2.0 |
| Purified water | 47.0 |
| Total | 100.00 |

Process:

Part A: Polaxamer 188 was heated until melted. Minocycline HCl was added to the molten polaxamer and mixed. This mixture was cooled and a solid mass was formed. This solid mass was screened and added to a portion of alcohol. Propyl gallate and butylated hydroxytoluene were dissolved in the balance of absolute alcohol.

Part B: Polyvinyl alcohol was dissolved in hot purified water and allowed to cool; and sodium sulfite was added under stirring until dissolved.

Part C: Part A and Part B were mixed under stirring. Triethyl citrate and isopropyl myristate were added and mixed well to form a homogenous mixture.

The film produced from the above formulation is characterized by the following properties:
1. Weight: 66 mg/10 sq cm (+/−10%).
2. Thickness: 0.056 mm (+/−10%)
3. Folding endurance measured as number of folds before rupture—not less than 150.
4. Tensile break: 627 gms/mm (+/−10%).

Example 2

Table 2 shows a formulation for a film-forming itraconazole gel, expressed as percent weight/weight (% w/w) of the composition.

TABLE 2

| Ingredients | % w/w |
| --- | --- |
| Itraconazole | 1.0 |
| Poloxamer 188 | 8.0 |
| Isoproyl alcohol | 20.5 |
| Polyvinyl alcohol | 15.0 |
| Propyl gallate | 0.1 |
| Tri ethyl citrate | 3.0 |
| Butylated hydroxyl toluene (BHT) | 0.4 |
| Isoproyl myristate | 2.0 |
| Purified water | 48.0 |
| Oleic acid | 2.0 |
| Total | 100.00 |

Process:

Part A: Polaxamer 188 was heated until melted. Itraconazole was added to the molten polaxamer and mixed. This mixture was cooled and a solid mass was formed. This solid mass was screened and added to a portion of alcohol. Propyl gallate and butylated hydroxytoluene were dissolved in the balance of absolute alcohol.

Part B: Polyvinyl alcohol was dissolved in hot purified water and allowed to cool and sodium sulfite was added under stirring until dissolved.

Part C: Part A and Part B were mixed under stirring. Triethyl citrate and isopropyl myristate were added and mixed well to form a homogenous mixture.

The film produced from the above formulation is characterized by the following properties:
1. Weight: 54 mg/10 sq cm (+/−10%).
2. Thickness: 0.057 mm (+/−10%)
3. Folding endurance measured as number of folds before rupture—not less than 150.
4. Tensile break: 1482 gms/mm (+/−10%).

Example 3

Table 3 shows a formulation for a film-forming lidocaine gel, expressed as weight/weight of the composition.

TABLE 3

| Ingredients | % w/w |
| --- | --- |
| Lidocaine | 5.0 |
| Poloxamer 188 | 8.0 |
| Absolute alcohol | 18.5 |
| Polyvinyl alcohol | 15.0 |
| Propyl gallate | 0.1 |
| Tri ethyl citrate | 3.0 |
| Butylated hydroxyl toluene | 0.4 |
| Isoproyl myristate | 2.0 |
| Purified water | 48.0 |
| Total | 100.00 |

Process:

Part A: Polaxamer 188 was heated until melted. Lidocaine was added to the molten polaxamer and mixed. This mixture was cooled and a solid mass was formed. This solid mass was screened and added to a portion of alcohol. Propyl gallate and butylated hydroxytoluene were dissolved in the balance of absolute alcohol.

Part B: Polyvinyl alcohol was dissolved in hot purified water and allowed to cool and sodium sulfite was added under stirring until dissolved.

Part C: Part A and Part B were mixed under stirring. Triethyl citrate and isopropyl myristate were added and mixed well to form a homogenous mixture.

The film produced from the above formulation is characterized by the following properties:
1. Weight: 63 mg/10 sq cm (+/−10%).
2. Thickness: 0.097 mm (+/−10%)
3. Folding endurance measured as number of folds before rupture—not less than 150.
4. Tensile break: 330 gms/mm (+/−10%).

Example 4

Table 4 shows the formulation for a film-forming diclofenac epolamine gel, expressed as weight/weight of the composition.

TABLE 4

| Ingredients | % w/w |
| --- | --- |
| Diclofenac epolamine | 1.3 |
| Poloxamer 188 | 8.0 |
| Absolute alcohol | 16.5 |
| Polyvinyl alcohol | 17.0 |
| Propyl gallate | 0.1 |
| Tri ethyl citrate | 3.0 |
| Butylated hydroxyl toluene | 0.4 |

TABLE 4-continued

| Ingredients | % w/w |
|---|---|
| Isoproyl myristate | 2.0 |
| Purified water | 51.7 |
| Total | 100.00 |

Process:

Part A: Polaxamer 188 was heated until melted. Diclofenac epolamine was added to the molten polaxamer and mixed. This mixture was cooled and a solid mass was formed. This solid mass was screened and added to a portion of alcohol. Propyl gallate and butylated hydroxytoluene were dissolved in the balance of absolute alcohol.

Part B: Polyvinyl alcohol was dissolved in hot purified water and allowed to cool and sodium sulfite was added under stirring until dissolved.

Part C: Part A and Part B were mixed under stirring. Triethyl citrate and isopropyl myristate were added and mixed well to form a homogenous mixture.

The film produced from the above formulation is characterized by the following properties:
1. Weight: 90 mg/10 sq cm (+/−10%).
2. Thickness: 0.063 mm (+/−10%)
3. Folding endurance measured as number of folds before rupture—not less than 150.
4. Tensile break: 485 gms/mm (+/−10%).

Example 5

Table 5 shows the formulation for a film-forming nicotine gel, expressed as weight/weight of the composition.

TABLE 5

| Ingredients | % w/w |
|---|---|
| Nicotine | 20.0 |
| Carrageenan | 1.0 |
| Absolute alcohol | 10.5 |
| Polyvinyl alcohol | 15.0 |
| Propyl gallate | 0.1 |
| Tri ethyl citrate | 3.0 |
| Butylated hydroxyl toluene | 0.4 |
| Purified water | 50.0 |
| Total | 100.00 |

Process:

Part A: Polyvinyl alcohol was dissolved in hot purified water and allowed to cool and carrageenan and nicotine were added until dissolved.

Part B: Propyl gallate and butylated hydroxytoluene were dissolved in absolute alcohol.

Part C: Part A and Part B were mixed under stirring. Triethyl citrate was added and mixed well to form a homogenous mixture.

The film produced from the above formulation is characterized by the following properties:
1. Weight: 93 mg/10 sq cm (+/−10%).
2. Thickness: 0.048 mm (+/−10%)
3. Folding endurance measured as number of folds before rupture—not less than 150.
4. Tensile break: 712 gms/mm (+/−10%).

TABLE 6

| Ingredients | % w/w |
|---|---|
| Minocycline HCL | 4.0 |
| Poloxamer 188 | 8.0 |
| Absolute alcohol | 15.5 |
| Polyvinyl alcohol | 15.0 |
| Sodium sulfite | 4.0 |
| Propyl gallate | 0.1 |
| Tri ethyl citrate | 3.0 |
| Butylated hydroxyl toluene | 0.4 |
| Isoproyl myristate | 2.0 |
| Purified water | 47.5 |
| Carbopol 971P | 0.5 |
| Total | 100.0 |

Part A: Polaxamer 188 was heated until melted. Minocycline HCl was added to the molten poloxamer and mixed. This mixture was cooled and a solid mass was formed. This solid mass was screened and added to a portion of alcohol. Propyl gallate and butylated hydroxytoluene were dissolved in the balance of absolute alcohol.

Part B: Polyvinyl alcohol was dissolved in hot purified water and allowed to cool and sodium sulfite and Carbopol 971P were added under stirring until dissolved.

Part C: Part A and Part B were mixed under stirring. Triethyl citrate and isopropyl myristate were added and mixed well to form a homogenous mixture.

The film produced from the above formulation is characterized by the following properties:
1. Weight: 60 mg/10 sq cm (+/−10%).
2. Thickness: 0.063 mm (+/−10%)
3. Folding endurance measured as number of folds before rupture—not less than 150.
4. Tensile break: 579 gms/mm (+/−10%).

While the present invention has been described with reference to the specific embodiments thereof, it should be understood by those skilled in the art that various changes may be made and equivalents may be substituted without departing from the true spirit and scope of the invention. In addition, many modifications may be made to adapt to a particular situation, material, composition of matter, process, process step or steps, to the objective, spirit and scope of the present invention. All such modifications are intended to be within the scope of the claims appended hereto.

What is claimed is:

1. A pharmaceutical composition for application directly to a site on skin or to a substrate for application directly to the site on skin comprising:
   (a) a therapeutic amount of an active agent, wherein the active agent is present at a concentration of at least 1% w/w of the composition;
   (b) a non-cellulosic polymer or copolymer selected from the group consisting of a poloxamer, an ethoxylated linear alcohol, a fatty acid ester, an amine derivative, an amide derivative, a polyglucoside, a polyalcohol, an ethoxylated polyalcohol and a thiol, wherein the non-cellulosic polymer or copolymer is present at a concentration from 1% to 30% w/w of the composition;
   (c) a film forming agent selected from the group consisting of polyvinyl alcohol, polyvinyl pyrrolidone (copovidone), carrageenan, gelatin, dextrin, polyethylene oxide, guar gum, xanthan gum, Tragacanth gum, hydroxyethyl cellulose, ethylcellulose, carboxymethylcellulose, hydroxypropylcellulose, polyvinyl alcohol-polyethylene glycol co-polymers, methyacrylic acid-ethyl acrylate copolymers, methacrylic acid, methacrylate based polymers, methylmethacrylate copolymers and a combination thereof, wherein the film forming agent is present at a concentration from 1% to 80% w/w of the composition;

(d) a plasticizer selected from the group consisting of N-methyl-2-pyrrolidone, glycerol formaldehyde, acetyltributylcitrate, ethanol, triacetin, triethyl citrate, acetyl triethyl citrate, tributyl citrate, acetyl tributyl citrate, trimethyl citrate, glycerin, sorbitol, polyethylene glycol, polypropylene glycol, polyethylene-propylene glycol, glycerol, glycerol monoacetate, diacetate or polysorbate, cetyl alcohol, and sodium diethylsulfosuccinate, wherein the plasticizer is present at a concentration from 1% to 20% w/w of the composition;

(e) a permeation enhancer selected from the group consisting of isopropyl palmitate, isopropyl myristate, isopropyl stearate, propylene glycol, octyl stearate, tridecyl neopentanoate, benzyl alcohol, linoleic acid, alpha-linolenic, oleic acid, cod liver-oil, methanol, menthol derivatives, squalene, glycerol derivatives, urea, sodium taurocholate and a combination thereof;

(f) an antioxidant selected from the group consisting of ascorbic acid (vitamin C), ascorbyl esters of fatty acids, magnesium ascorbyl phosphate, sodium ascorbyl phosphate, ascorbyl sorbate, tocopherol (vitamin E), tocopherol sorbate, tocopherol acetate, butylated hydroxyl benzoic acid, 6-hydroxy-2,5,7,8-tetramethyl-chroman-2-carboxylic acid, gallic acid, propyl gallate, uric acid, sorbic acid, lipoic acid, N,N-diethylhydroxylamine, amino-guanidine, glutathione, dihydroxy fumaric acid, glycine pidolate, arginine pilolate, nordihydroguaiaretic acid, bioflavonoids, curcumin, lysine, methionine, proline, cysteine, superoxide dismutase, silymarin, tea extracts, grape skin/seed extracts, melanin, rosemary extracts, sodium bisulfite, sodium sulfite, butylated hydroxytoluene (BHT) and butylated hydroxyanisole (BHA), wherein the antioxidant is present at a concentration form 0.1% to 10% w/w of the composition; and (g) water to bring the composition to 100% w/w, wherein the pharmaceutical composition when applied is in form of a gel and the gel forms a film in-situ, and the composition being characterized by A. controlled release at locally sustained levels of a minimum effective concentration (MEC) of the active agent with maintained potency;

B. the film that is effective to conform to a surface of the skin during movement without breaking of the film, wherein tensile break ranges from 297 gms/mm to 1630 gms/mm;

C. the film that is of a quality or tendency to bend that does not require force or pressure from the outside;

D. the film that can be removed from the skin by peeling without leaving a substantial residue; and E. the film that forms on skin can be applied to a site on skin of any size.

2. The topical film-forming pharmaceutical composition according to claim 1, wherein the active agent is an analgesic agent, an anesthetic agent; an anti-acne agent; an anti-aging agent, an antibiotic agent; an anti-fungal agent; an anti-histamine, an anti-inflammatory agent (steroidal and non-steroidal); a nicotinic cholinergic receptor agonist, an anti-oxidant agent; an anti-protozoal agent; an anti-pruritic agent; an anti-viral agent; a chemotherapeutic agent, an immunomodulatory agent, a keratolytic agent, or a retinoid.

3. The topical film forming pharmaceutical composition according to claim 1, wherein the active agent is an antibiotic.

4. The topical film-forming composition according to claim 2, wherein the antibiotic is a beta-lactam, a cephalosporin, a fluoroquinolones, an aminoglycoside, a monobactam, a carbapenem, a macrolide, or a tetracycline, a natural or synthetic anti-infective peptide, a glycosylated, phosphorylated, or glycosylated and phosphorylated derivative of a natural or synthetic anti-infective peptide, or an anti-infective monoclonal antibody cocktail.

5. The topical film forming pharmaceutical composition according to claim 3, wherein the antibiotic is a tetracycline antibiotic.

6. The topical film forming pharmaceutical composition according to claim 4, wherein the tetracycline antibiotic is minocycline.

7. The topical film forming pharmaceutical composition according to claim 1, wherein the active agent is an anti-fungal agent.

8. The topical film forming pharmaceutical composition according to claim 5, wherein the anti-fungal agent is itraconazole.

9. The topical film-forming pharmaceutical composition according to claim 2, wherein the nicotinic cholinergic receptor agonist is nicotine.

10. The topical film-forming pharmaceutical composition according to claim 2, wherein the retinoid is isotretinoin.

11. The topical film-forming pharmaceutical composition according to claim 1, wherein the plasticizer is selected from the group consisting of triacetine, triethyl citrate, acetyl triethyl citrate, tributyl citrate, acetyl tributyl citrate, trimethyl citrate, other citrate esters, glycerin, sorbitol, a polyethylene glycol, a polypropylene glycol, a polyethylene-propylene glycol, glycerol, glycerol monoacetate, glycerol diacetate, glycerol polysorbate, cetyl alcohol, and sodium diethylsulfosuccinate.

12. The topical film-forming composition according to claim 1, wherein the antioxidant is selected from the group consisting of alpha tocopherol (Vitamin-E), ascorbic acid, ascorbic acid esters, glutathione, lipoic acid, uric acid, carotenes, propyl gallate, sodium bisulfite, sodium sulfite, butylated hydroxytoluene (BHT), butylated hydroxyanisole (BHA), and cysteine.

13. The topical film-forming composition according to claim 1, wherein the active agent is present at a concentration ranging from 1% to 60% w/w.

14. The topical film-forming composition according to claim 1, wherein the substrate is a backing material.

15. The topical film-forming composition according to claim 14, wherein the backing material substrate is occlusive.

16. The topical film-forming composition according to claim 14, wherein the backing material substrate is nonocclusive.

17. The topical bioadhesive film-forming pharmaceutical composition according to claim 1, the composition further comprising one or more excipients selected from the group consisting of a preservative, a solubilizer, a phase transfer catalyst, a viscosity modifier, a vitamin, a mineral nutrient, a solvent, a colorant and a fragrance.

18. The topical film-forming composition according to claim 17, wherein the solvent is selected from the group consisting of polyhydric alcohol, glycerin, ethylene glycol, dipropylene glycol, hexylene glycol, and mixtures thereof.

19. The topical film-forming composition according to claim 17, wherein the solvent is present at a concentration ranging from 10% to 90% w/v.

* * * * *